United States Patent [19]

Yoon

[11] Patent Number: 5,693,059

[45] Date of Patent: Dec. 2, 1997

[54] LIGATING INSTRUMENT WITH MULTIPLE LOOP LIGATURE SUPPLY AND METHODS THEREFOR

[76] Inventor: InBae Yoon, 2101 Highland Ridge Dr., Phoenix, Md. 21131

[21] Appl. No.: 531,153

[22] Filed: Sep. 15, 1995

[51] Int. Cl.$^6$ ........................................... A61B 17/10
[52] U.S. Cl. .................. 606/139; 606/144; 606/146
[58] Field of Search ..................... 606/139, 146, 606/102, 113, 144, 148

[56] References Cited

U.S. PATENT DOCUMENTS

| | | |
|---|---|---|
| 2,227,270 | 1/1940 | Moore . |
| 2,610,631 | 11/1952 | Calicchio . |
| 2,856,933 | 1/1958 | Hildebrand et al. . |
| 3,033,204 | 5/1962 | Wood . |
| 3,580,256 | 5/1971 | Wilkinson . |
| 3,871,379 | 3/1975 | Clarke . |
| 4,018,229 | 4/1977 | Komiya . |
| 4,387,489 | 6/1983 | Dudek . |
| 4,592,355 | 6/1986 | Antebi . |
| 4,935,027 | 6/1990 | Yoon . |
| 5,019,049 | 5/1991 | Haining . |
| 5,078,731 | 1/1992 | Hayhurst . |
| 5,133,723 | 7/1992 | Li et al. . |
| 5,160,339 | 11/1992 | Chen et al. . |
| 5,163,942 | 11/1992 | Rydell . |
| 5,171,259 | 12/1992 | Inoue . |
| 5,196,022 | 3/1993 | Bilweis . |
| 5,217,024 | 6/1993 | Dorsey et al. ............... 128/758 |
| 5,236,434 | 8/1993 | Callicrate . |
| 5,242,459 | 9/1993 | Buelna . |
| 5,281,238 | 1/1994 | Chin et al. . |
| 5,282,809 | 2/1994 | Kammerer et al. . |
| 5,290,284 | 3/1994 | Adair . |
| 5,300,078 | 4/1994 | Buelna . |
| 5,306,280 | 4/1994 | Bregen et al. ............... 606/143 |
| 5,312,423 | 5/1994 | Rosenbluth et al. . |
| 5,318,578 | 6/1994 | Hasson . |
| 5,320,629 | 6/1994 | Noda et al. . |

(List continued on next page.)

FOREIGN PATENT DOCUMENTS 0477020  3/1992  European Pat. Off. .

OTHER PUBLICATIONS

Port Saver PercLoop by Advanced Surgical, Inc. Features and Bene Benefits and Specifications.
Berry and Kohn's Introduction to Operating Room Technique, McGraw–Hill Book Company.

Primary Examiner—Michael Buiz
Assistant Examiner—Tina T. D. Pham

[57] ABSTRACT

A ligating instrument for forming ligatures at an internal operative site in the body includes an instrument body having a distal end for positioning at the operative site, a proximal end for positioning externally of the body and a lumen between the distal and proximal ends. A ligature supply including a plurality of preformed, contractible ligature loops of filamentous ligature material is disposed in the lumen. Each of the ligature loops has a fixed knotting element and a movement permitting knotting element permitting movement of the ligature material relative thereto to reduce the size of the ligature loops around anatomical structure. The ligature supply is movable distally relative to the instrument body to move a ligature loop through the distal end to deploy the ligature loop externally of the instrument body for positioning around anatomical structure. An operating member carried by the instrument body is operable to move the ligature material proximally relative to the instrument body to reduce the size of the ligature loop around the anatomical structure to form a ligature while the movement permitting knotting element of the ligature loop is maintained externally of the instrument body. A method of forming ligatures includes the steps of withdrawing a ligature loop of filamentous material through a distal end of an instrument body, positioning the ligature loop around anatomical structure, moving an operating member to move the filamentous material proximally relative to the instrument body to reduce the size of the ligature loop around the anatomical structure to form a ligature and withdrawing another ligature loop of the ligature supply through the distal end of the instrument body to form another ligature.

30 Claims, 24 Drawing Sheets

U.S. PATENT DOCUMENTS

| | | |
|---|---|---|
| 5,330,491 | 7/1994 | Walker et al. . |
| 5,334,199 | 8/1994 | Yoon . |
| 5,336,231 | 8/1994 | Adair . |
| 5,383,882 | 1/1995 | Buess et al. . |
| 5,383,905 | 1/1995 | Golds et al. . |
| 5,403,331 | 4/1995 | Chesterfield et al. . |
| 5,445,167 | 8/1995 | Yoon et al. ............... 128/898 |
| 5,454,820 | 10/1995 | Kammerer et al. ............... 606/148 |

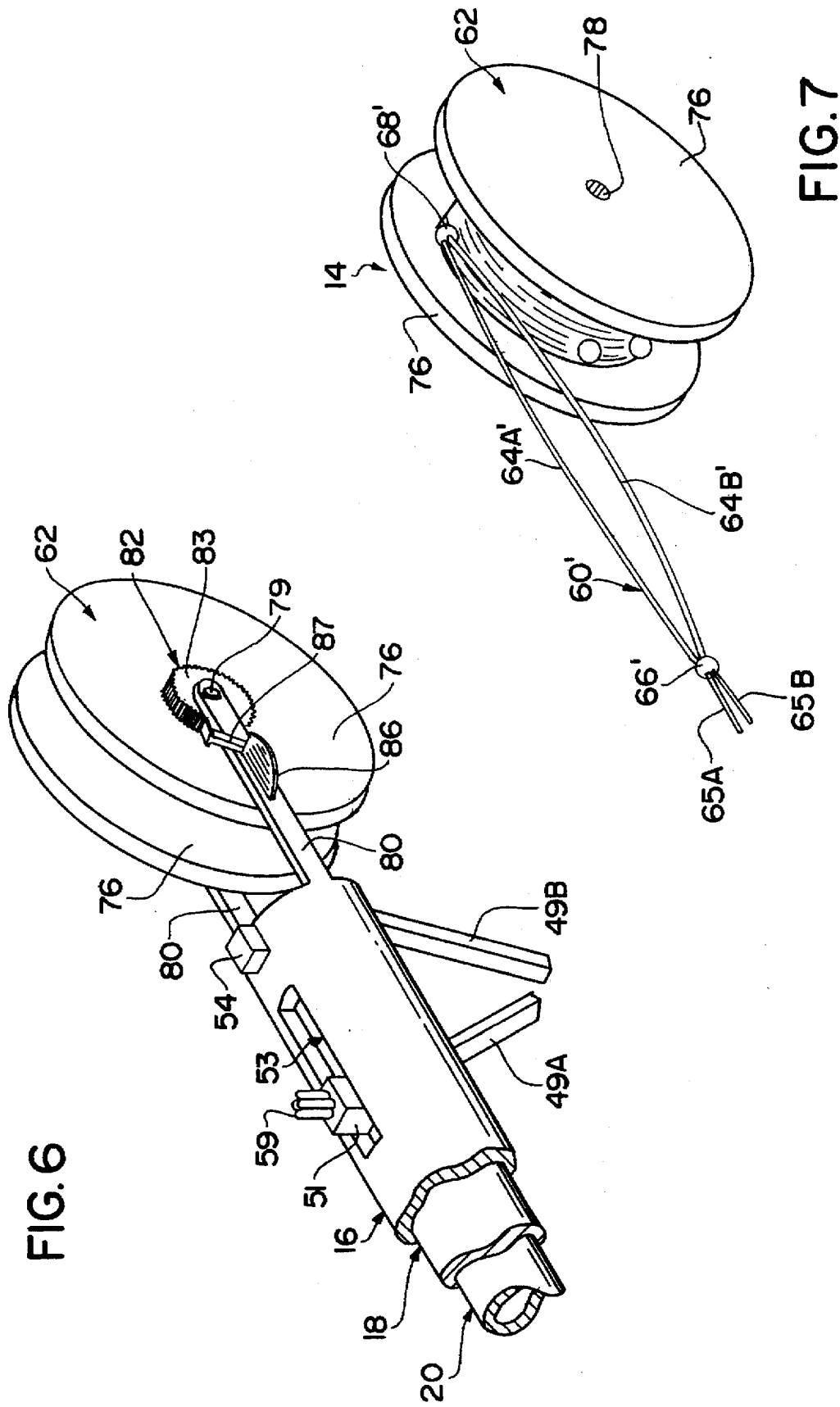

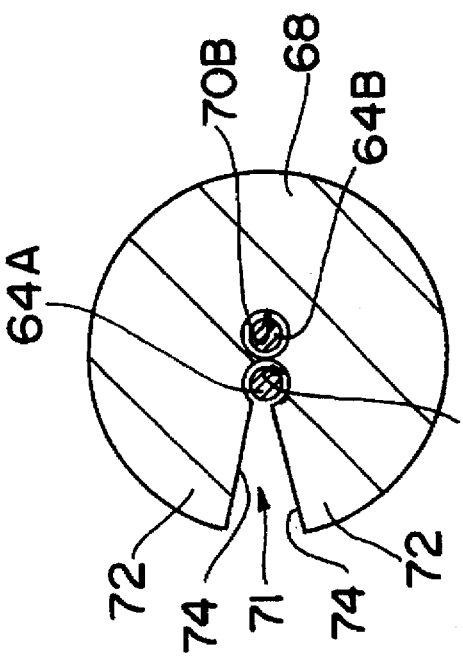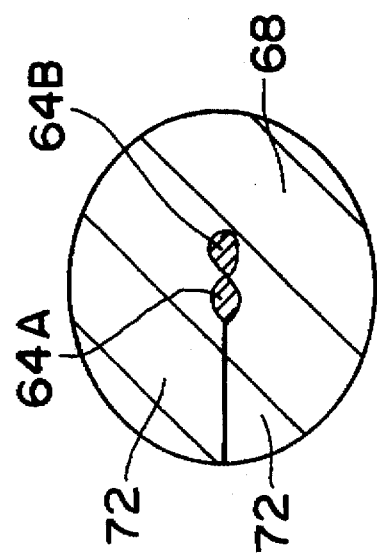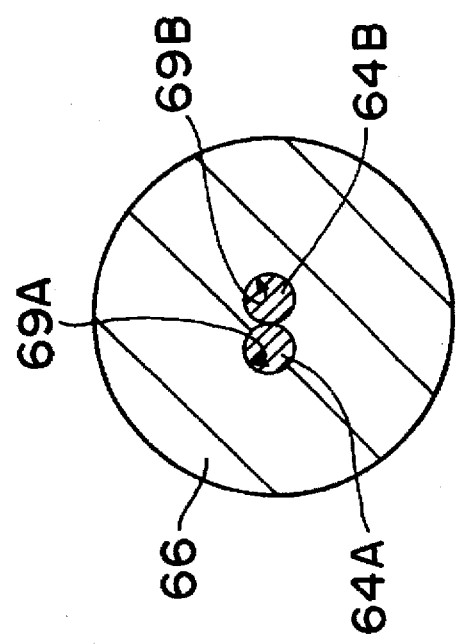

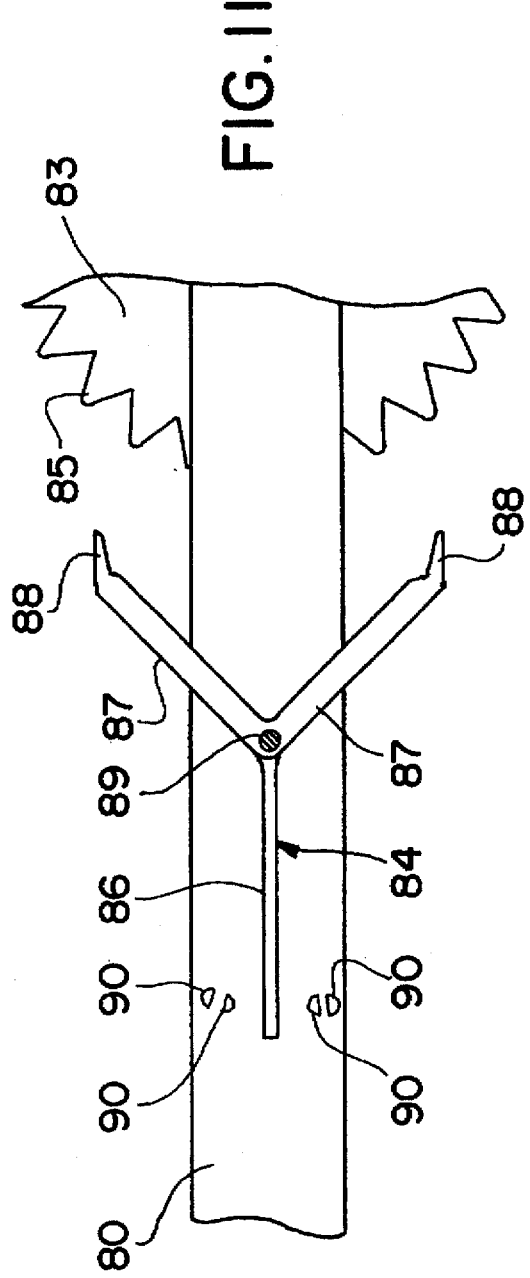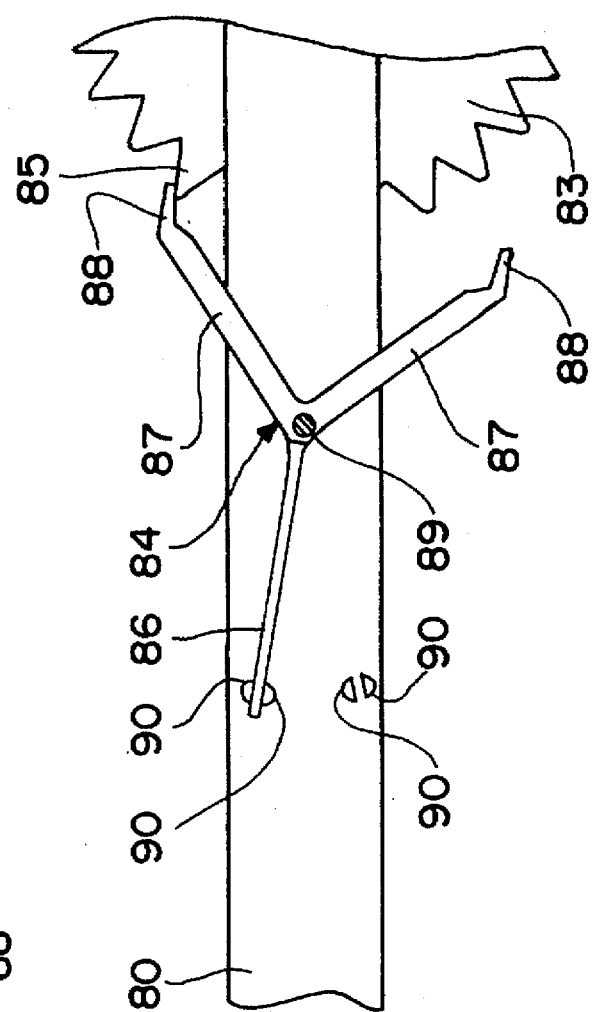

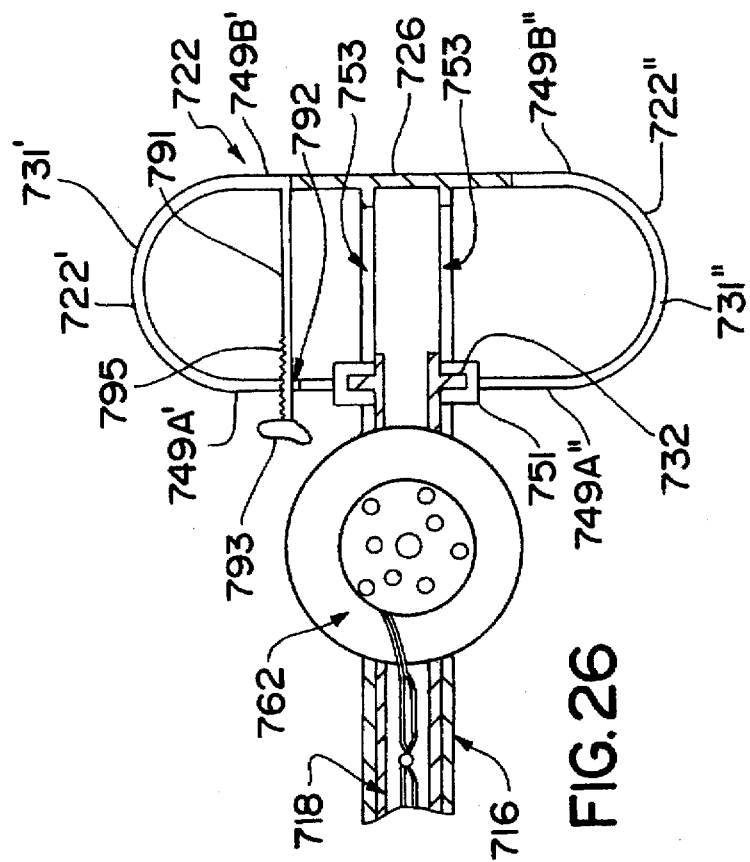
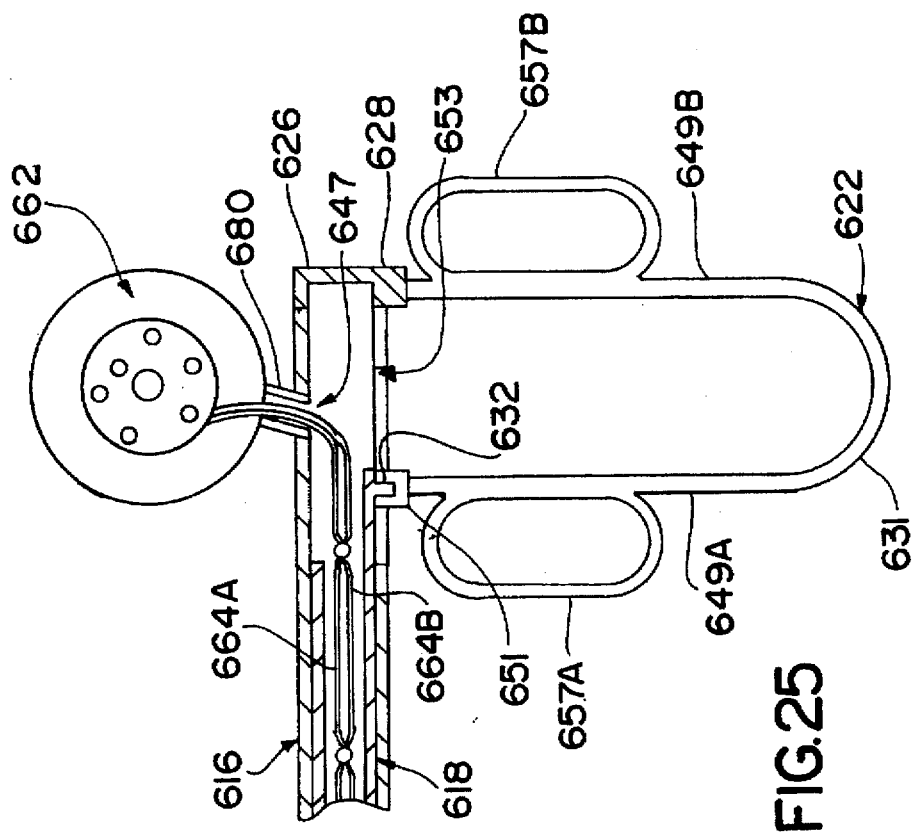
FIG. 26
FIG. 25

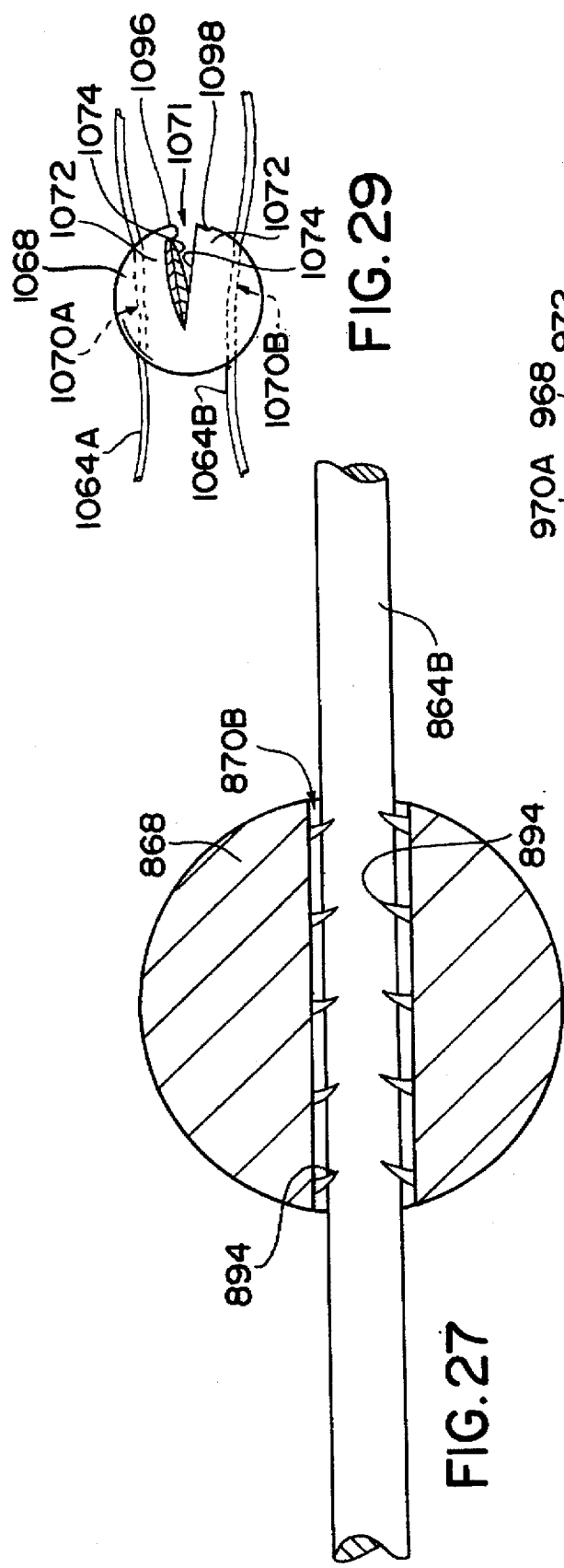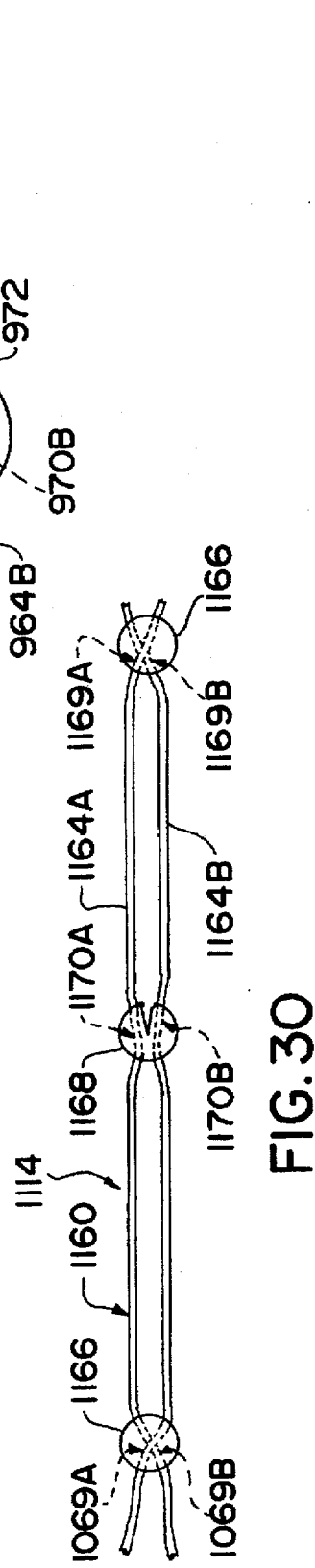

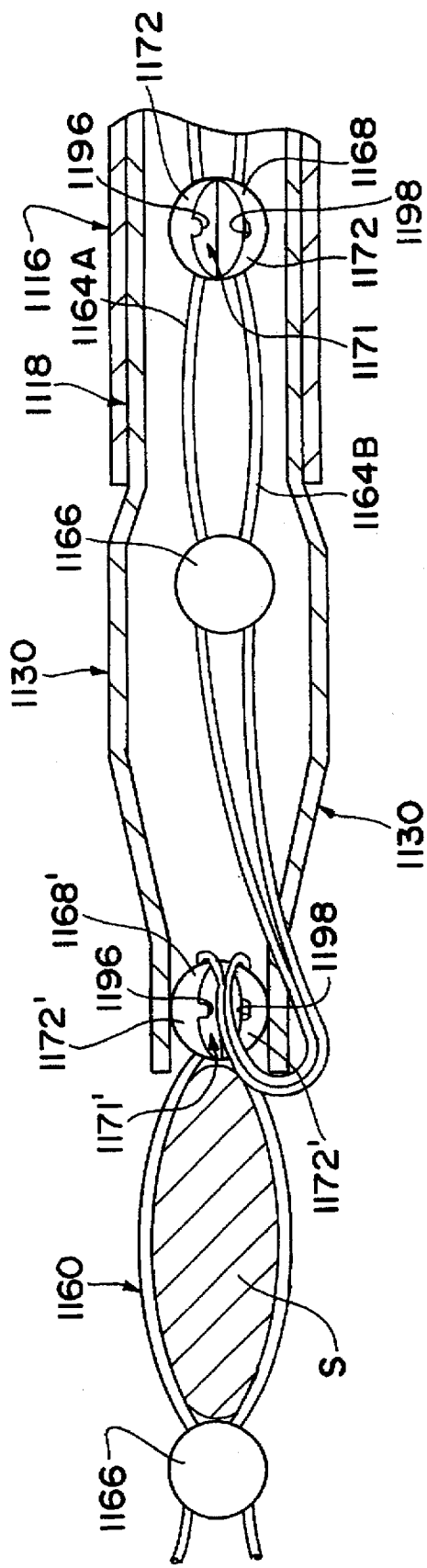
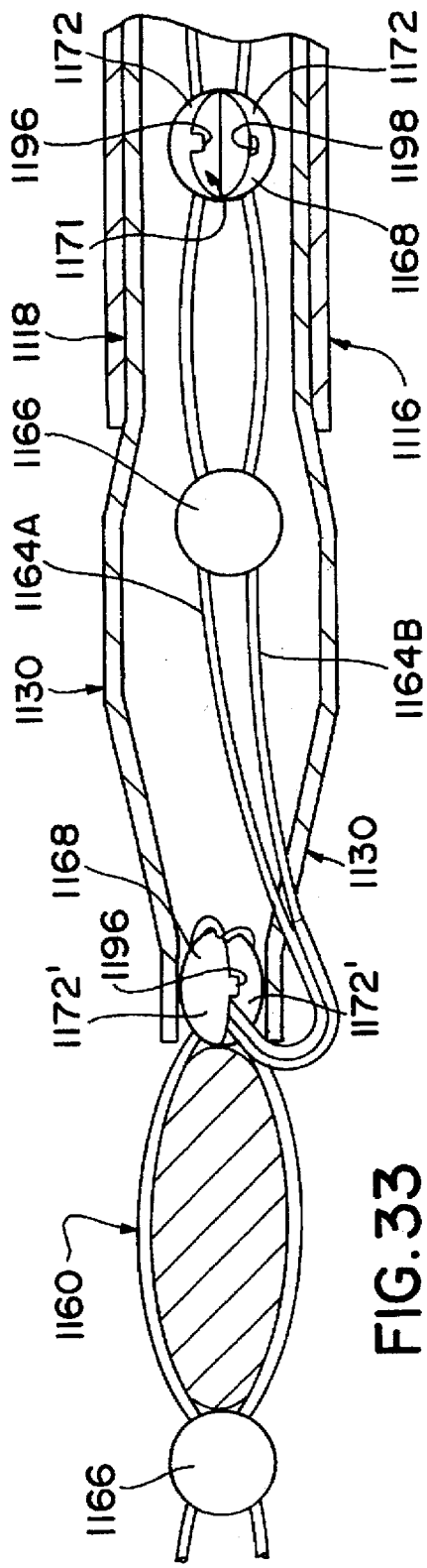
FIG. 32
FIG. 33

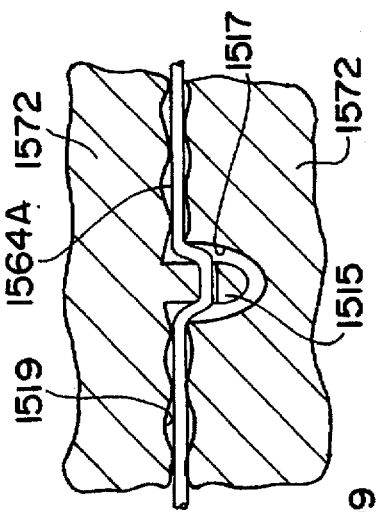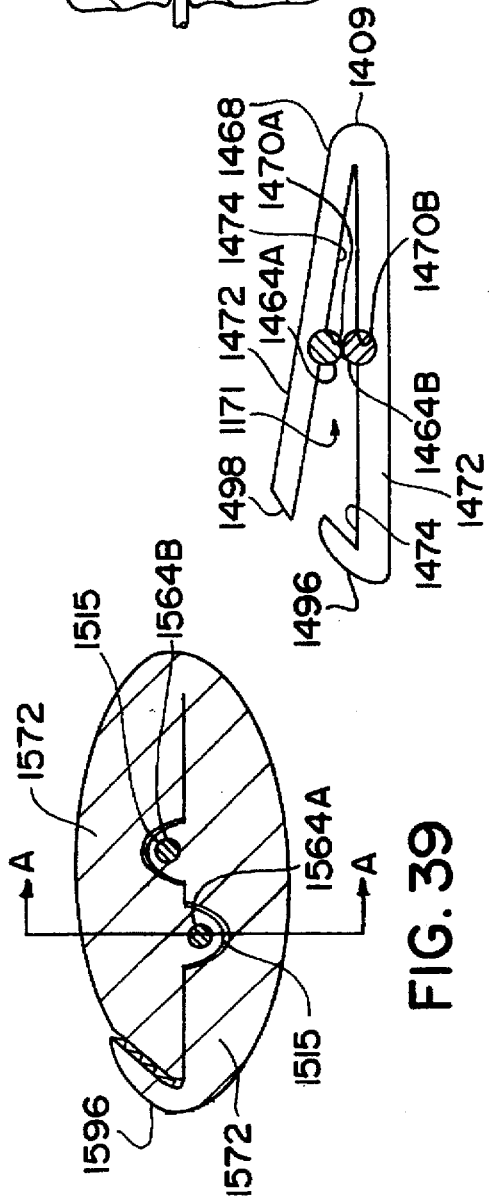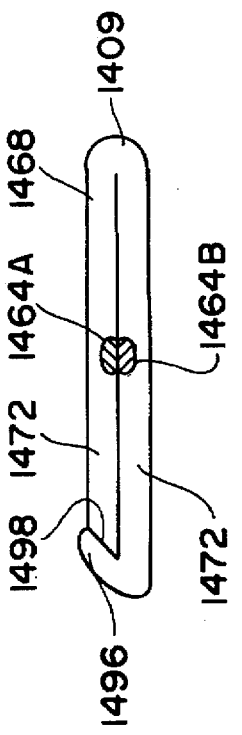

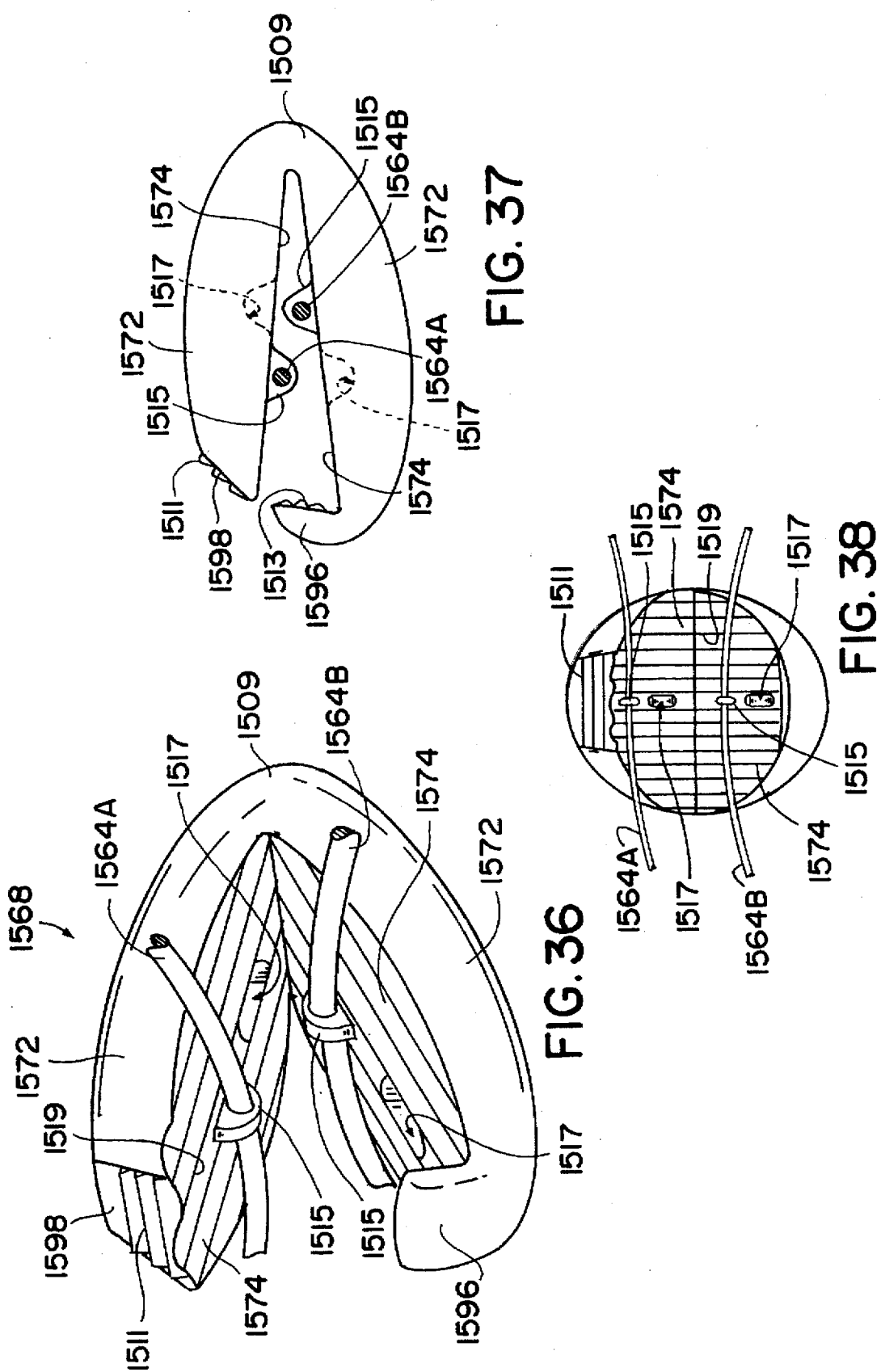

LIGATING INSTRUMENT WITH MULTIPLE LOOP LIGATURE SUPPLY AND METHODS THEREFOR

BACKGROUND OF THE INVENTION

1. Field of the Invention

The present invention pertains to ligating instruments and, more particularly, to ligating instruments operable with one hand for use in endoscopic and non-endoscopic operative procedures and to methods therefor.

2. Discussion of the Prior Art

Closed or endoscopic operative procedures, also known as least-invasive procedures, have become extremely popular for use in many areas such as laparoscopy (pelviscopy), gastroentroscopy, laryngobronchoscopy and arthroscopy. In endoscopic operative procedures, access to an internal operative site in the body is gained through a relatively narrow or small size endoscopic portal establishing communication with the internal operative site from externally of the body. Accordingly, various instruments can be introduced at the operative site via the portal without the need for a skin incision of substantial size as is typically required for open procedures. Endoscopic procedures provide many benefits over open procedures including minimal invasiveness and trauma, fewer complications, shorter wound healing times, less patient discomfort, shorter hospitalization and rehabilitation times, cost savings and the ability to perform surgery without general anesthesia and in non-hospital or out-patient sites.

Ligating or tying anatomical tissue or organ structure is a time consuming and tedious part of both endoscopic and non-endoscopic operative procedures due to the difficulty involved in tying or applying an occluding ligature to anatomical tissue or other anatomical structure as is desirable and/or necessary in many various procedures. Ligating anatomical tissue is particularly difficult in endoscopic procedures due to the constraints on access to the operative site, the limited room for maneuverability at the operative site and the procedural or operational complexity required of many conventional endoscopic ligating instruments. Accordingly, the advantages of endoscopic procedures are sometimes outweighed by the disadvantages caused by the increased difficulty to ligate or tie and the increased length of time required to perform endoscopic procedures where such time is significantly extended due to the time required for ligation or tying.

Because endoscopic procedures are preferred over open procedures, much effort has been spent to develop instruments and techniques for facilitating tissue ligation. One technique involves the use of a ligating device, such as the Endoloop™ manufactured by Ethicon Endo-Surgery Inc. Various other ligating devices or instruments have been proposed, as exemplified by U.S. Pat. No. 5,383,882 to Buess et al, No. 5,336,231 to Adair, No. 5,334,199 to Yoon, No. 5,300,078 to Buelna, No. 5,290,284 to Adair, No. 5,281,238 to Chin et al, No. 5,242,459 to Buelna, No. 5,236,434 to Callicrate and No. 2,610,631 to Calicchio.

Many presently available ligating devices, instruments and procedures have various disadvantages including structural and operational complexity, tedious, difficult and time consuming procedural steps, the need for two-handed operation, the inability to sense or "feel" desired ligature tension and the inability to form multiple ligatures or ties without withdrawing the ligating devices or instruments from the body.

SUMMARY OF THE INVENTION

Accordingly, it is a primary object of the present invention to overcome the disadvantages of prior art ligating devices, instruments and procedures.

Another object of the present invention is to utilize a ligating instrument to form a plurality of ligatures at an internal operative site in the body without withdrawal of the ligating instrument from the body.

A further object of the present invention is to provide a ligating instrument including an elongate instrument body and a ligature supply including a plurality of preformed, contractible ligature loops of filamentous ligature material and having knotting elements permitting movement of the ligature material relative to the knotting elements to contract the ligature loops around anatomical structure to form ligatures.

An additional object of the present invention is to move the distal end of the instrument body from a closed position preventing passage of the knotting elements therethrough to an open position permitting passage of the knotting elements therethrough to position a ligature loop, including the knotting element thereof, externally of the distal end.

It is also an object of the present invention to move an operating member at the proximal end of the insturment body to move the ligature material proximally relative to the instrument body with the distal end in the closed position to contract the ligature loop around anatomical structure to form a ligature.

The present invention has as a further object to fix the knotting element of the tightened ligature loop to the ligature material to prevent expansion of the ligature.

Yet another object of the present invention is to cut the ligature material proximally of the ligature to permit another ligature loop, including the knotting element thereof, to be positioned externally of the distal end to form another ligature without withdrawing the ligating instrument from the body.

Some of the advantages of the present invention are that ligating anatomical structure is facilitated in both endoscopic and non-endoscopic procedures, the ligating instruments are operable with a single hand to form a plurality of ligatures, various diverse ligature supplies can be coupled with an instrument body allowing the optimal ligature supply to be selected in accordance with procedural use, ligatures can be formed in anatomical structure with a desired tension as tactilely sensed via the operating member, cutting of the ligature material proximally of the ligatures can be accomplished simultaneously with fixing of the knotting elements to the ligature material, the knotting elements can be fixed to more than one segment of the ligature material for redundant protection or securement of the ligatures, and the distal end of the ligating instrument can be utilized as a conductive element to treat tissue with energy.

These and other objects, advantages and benefits are realized with the present invention as generally characterized in a ligating instrument comprising an elongate instrument body and a ligature supply coupled with the instrument body. The instrument body has a distal end for positioning at an internal operative site in the body, a proximal end for positioning externally of the body, a lumen between the distal and proximal ends and a handle coupled with the proximal end for moving the distal end between a closed position, wherein the distal end defines a first size passage communicating with the lumen, and an open position, wherein the distal end defines a second, greater size passage communicating with the lumen. The ligature supply includes a plurality of preformed, ligature loops of filamentous ligature material disposed in the lumen and an operating member at the proximal end of the instrument body for moving the ligature material longitudinally relative to the instrument body. Each of the ligature loops has a knotting element permitting movement of the ligature material relative thereto to reduce the size of the ligature loops around anatomical structure. The knotting elements and ligature material have configurations or sizes, respectively, permitting passage of both the knotting elements and the ligature material through the distal end when the distal end is in the open position and permitting passage of the ligature material but not the knotting elements therethrough when the distal end is in the closed position. The handle is operable to move the distal end between the closed position and the open position. With the distal end in the open position, the ligature material is movable distally relative to the instrument body and through the passage to position a ligature loop, including the knotting element thereof, externally of the instrument body for positioning around anatomical structure. With the distal end in the closed position, the operating member is movable to move the ligature material proximally relative to the instrument body to tighten or reduce the size of the ligature loop around the anatomical structure to form a ligature while the knotting element thereof is prevented from entering the passage. The distal end of the instrument body is operable via the handle to fix the knotting element to the ligature material to secure the ligature. The instrument body can include a cutter for cutting the ligature material proximally of the ligature, and the cutter is movable from a non-cutting position to a cutting position to cut the ligature material subsequent to or simultaneously with fixing of the knotting element to the ligature material.

A method of forming ligatures in anatomical structure according to the present invention includes the steps of introducing the distal end of the instrument body at the internal operative site, withdrawing a ligature loop from the distal end of the instrument body to position the ligature loop, including the knotting element thereof, externally of the instrument body, positioning the ligature loop around anatomical structure, moving the operating member to move the ligature material proximally relative to the instrument body to reduce the size of the ligature loop around the anatomical structure to form a ligature, and withdrawing another ligature loop from the distal end of the instrument body to form another ligature without withdrawing the ligating instrument from the body.

Other objects and advantages of the present invention will become apparent from the following description of the preferred embodiments taken in conjunction with the accompanying drawings, wherein like parts in each of the several figures are identified by the same reference characters.

BRIEF DESCRIPTION OF THE DRAWINGS

FIG. 6 is a broken perspective view of a proximal portion of the ligating instrument.

FIG. 7 is a perspective view of the multiple loop ligature supply of the ligating instrument.

FIG. 8 is a front sectional view of a knotting element fixed to the lengths of ligature material of the multiple loop ligature supply.

FIG. 9 is a front sectional view of a movement permitting knotting element disposed along the lengths of ligature material to allow a ligature loop of the multiple loop ligature supply to be reduced in size.

FIG. 10 is a front sectional view of the movement permitting knotting element after being plastically deformed to fix the position thereof along the lengths of ligature material.

FIG. 11 is a broken, side plan view of a rotational control mechanism of the ligating instrument showing the rotational control mechanism in a neutral position.

FIG. 12 is a broken, side plan view of the rotational control mechanism showing the rotational control mechanism in a first locked position.

FIG. 25 is a broken side view, partly in section, of an additional modification of a handle arrangement and an additional alternative arrangement for the instrument body and the ligature supply for the ligating instruments of the present invention.

FIG. 26 is a broken side view, partly in section, of a further modification of a handle arrangement for the ligating instruments of the present invention.

FIG. 27 is a broken, side sectional view of a modification of a knotting element for the ligature supplies according to the present invention.

FIG. 28 is a broken side view of another modification of a knotting element for the ligature supplies according to the present invention.

FIG. 29 is a broken side view of another modification of a knotting element for the ligature supplies according to the present invention.

FIG. 30 is a broken side view of a modification of a ligature supply according to the present invention.

FIG. 32 is a broken side view, partly in section, of a distal portion of a ligating instrument incorporating a ligature supply similar to the ligature supply of FIG. 30.

FIG. 33 is a broken side view, partly in section, showing a movement permitting knotting element of the ligating instrument of FIG. 32 being moved to a closed position to secure a ligature.

FIG. 34 is a side view of another modification of a knotting element for the ligature supplies of the present invention showing the knotting element in an open position.

FIG. 35 is a side view of the knotting element of FIG. 34 showing the knotting element in a closed position.

FIG. 36 is a broken perspective view of a further modification of a knotting element for the ligature supplies according to the present invention showing the knotting element in an open position.

FIG. 37 is a side view of the knotting element of FIG. 36.

FIG. 38 is a front view of the knotting element of FIG. 36.

FIG. 39 is a side view of the knotting element of FIG. 36 showing the knotting element in a closed position.

FIG. 40 is a broken sectional view taken along line A—A of FIG. 39.

DESCRIPTION OF THE PREFERRED EMBODIMENTS

Figure 1:
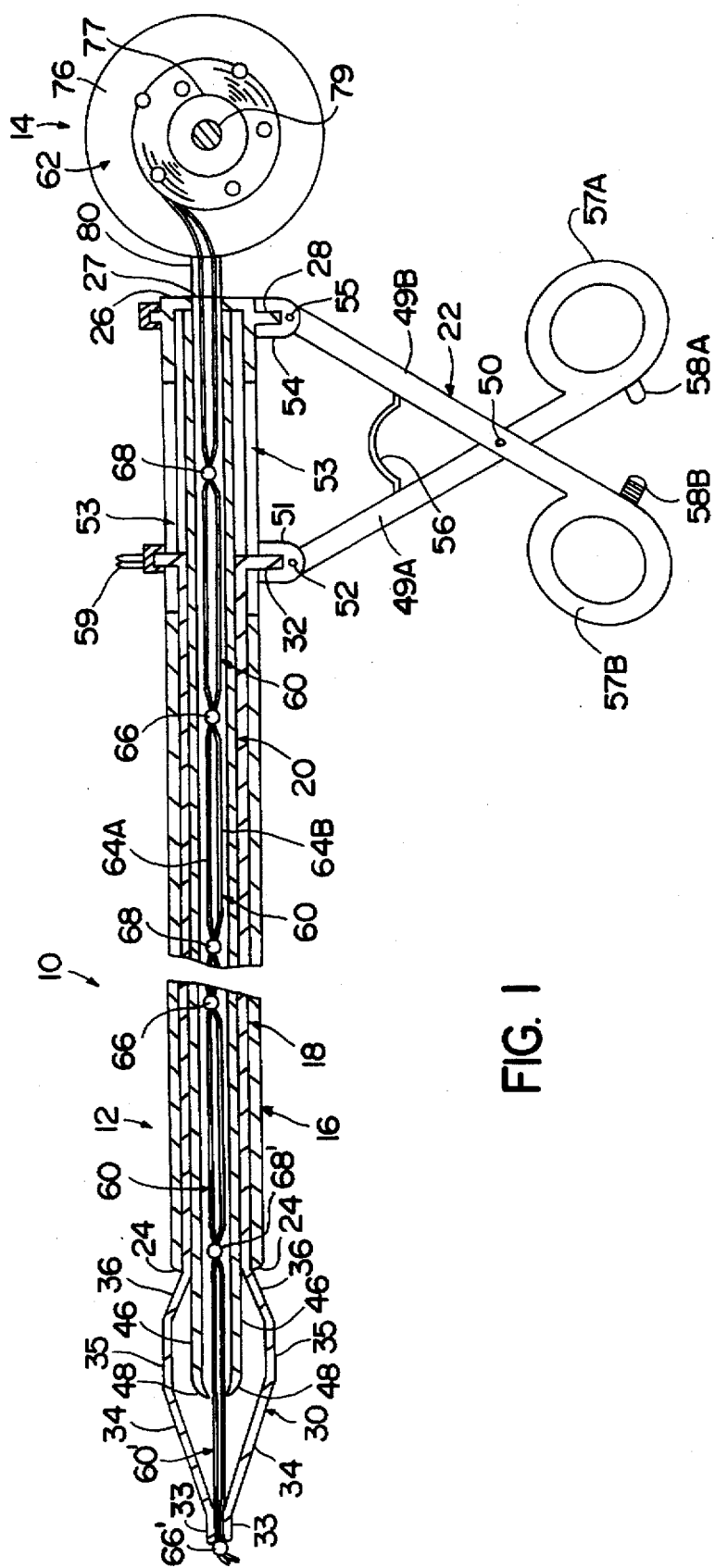
FIG. 1 is a broken side view, partly in section, of a ligating instrument according to the present invention.

A ligating instrument 10 according to the present invention is illustrated in FIG. 1 and includes an instrument body 12 and a multiple loop ligature supply 14 coupled with the instrument body. The instrument body 12 includes an elongate outer member 16, an elongate middle, jaw, fixating or forceps member 18 slidably disposed in outer member 16, an elongate inner member or cutter 20 slidably disposed in middle member 18 and a handle 22 mounting the outer, middle and inner members. Outer member 16 comprises a tubular or hollow body terminating distally at an open distal end 24 and proximally at a proximal end including a transverse end wall 26. Outer member 16 has a lumen between the distal and proximal ends communicating with a central aperture 27 in end wall 26. The outer member 16 preferably has an external diameter or cross-sectional size sufficiently small to be introduced at an internal operative site in the body through a relatively small size or narrow endoscopic portal for use in endoscopic procedures wherein the endoscopic portal establishes communication with the internal operative site from externally of the body. The proximal end of the outer member is configured as or provided with a transverse or radially extending flange 28 coupled with handle 22 as explained further below. As shown in FIGS. 2-5, an external or outer surface of the outer member is provided with a scale 29 for taking measurements in the body. Scale 29 includes indicia lines located incremental distances from the outer member distal end 24 and/or from one another, such distances being known to the surgeon or being visually indicated by numerals on the external surface of the outer member. As shown in FIGS. 2-5, scale 29 includes thick indicia lines extending entirely around the outer member and spaced from one another an incremental distance, for example, 0.5 cm, 1 cm, or 2 cm, and thin indicia lines extending entirely around the outer member and located one-half the incremental distance from the thick lines. With the scale 29, measurements can be taken in the body, as is frequently desirable, by comparing or aligning the object being measured with the known distances of the scale.

Figure 2:
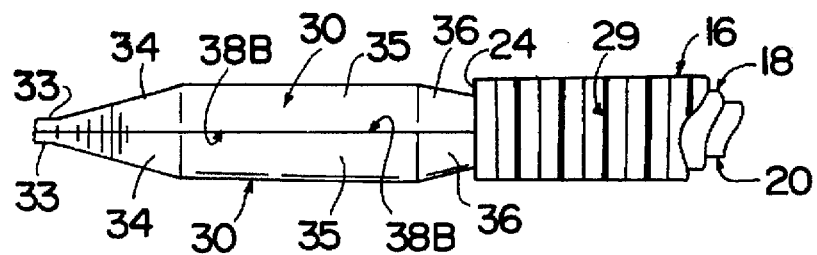
FIG. 2 is a broken side view of a distal portion of the ligating instrument showing the jaws in a closed position.
Figure 3:
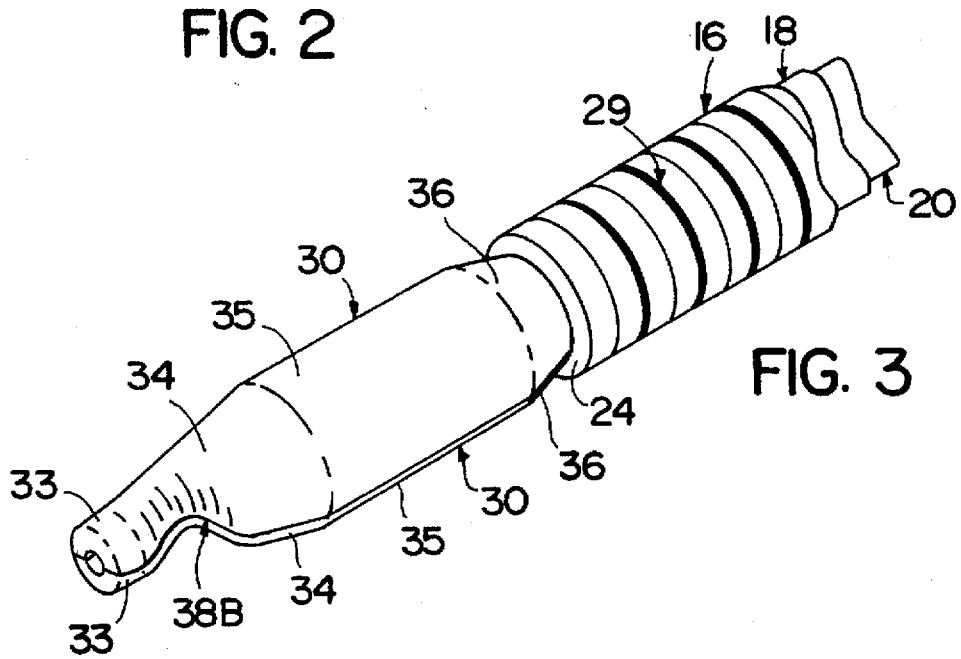
FIG. 3 is a broken perspective view of the distal portion of the ligating instrument.
Figure 4:
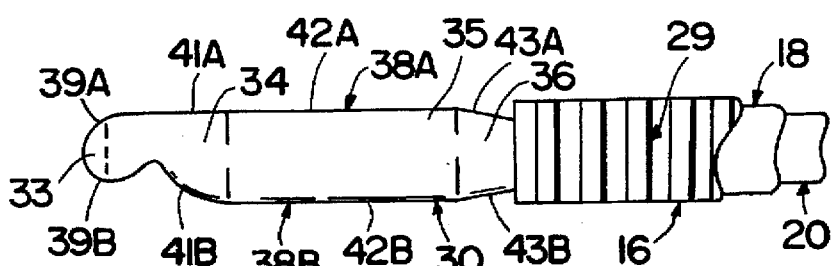
FIG. 4 is a broken, top plan view of the distal portion of the ligating instrument.
Figure 5:
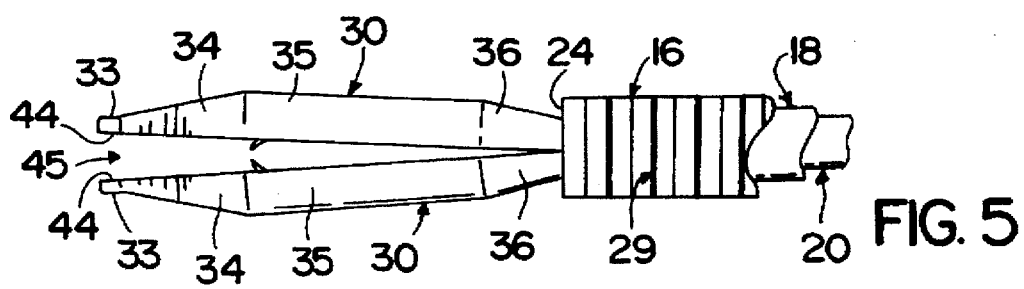
FIG. 5 is a broken side view of the distal portion of the ligating instrument showing the jaws in an open position.

The middle member 18 comprises a tubular or hollow body and a pair of opposed jaws 30 extending distally from the middle member body. The middle member body preferably has an external diameter or cross-sectional size to be closely received within the outer member 16 while allowing the outer and middle members to be moved longitudinally relative to one another. The middle member body terminates proximally at an open proximal end configured as or provided with a transverse or radially extending flange 32 coupled with handle 22 as explained further below. Each jaw 30 includes a tip or forward section 33, a forward intermediate section 34, a rearward intermediate section 35 and a rearward section 36. As shown in side view in FIG. 2 and in perspective view in FIG. 3, each tip section 33 includes a wall extending longitudinally from a rounded distal end of the corresponding jaw to the forward intermediate section 34. Each forward intermediate section 34 extends proximally from the corresponding tip section 33 and includes a wall extending angularly outwardly from the corresponding tip section in a direction away from a longitudinal axis of the middle member such that the forward intermediate sections are of increasing height along the length thereof in a proximal direction. Each rearward intermediate section 35 includes a wall extending longitudinally, proximally from the corresponding forward intermediate section 34 such that the rearward intermediate sections are of uniform height along the length thereof. Each rearward section 36 extends proximally from the corresponding rearward intermediate section 35 and includes a wall extending angularly inwardly from the corresponding rearward intermediate section in the direction of the middle member longitudinal axis such that the rearward sections are of decreasing height along the length thereof in a proximal direction and merge with the middle member body. As shown in FIG. 3 and in top view in FIG. 4, each jaw 30 includes opposing lateral edges 38A and 38B. Lateral edge 38A includes a curved tip edge section 39A, a straight forward intermediate edge section 41A extending proximally from tip edge section 39A parallel or substantially parallel with the middle member longitudinal axis, a straight rearward intermediate edge section 42A extending proximally from the forward intermediate edge section 41A parallel or substantially parallel with the middle member longitudinal axis and a straight rearward edge section 43A extending inwardly in the direction of the middle member longitudinal axis from the rearward intermediate edge section 42A to the middle member body. Lateral edge 38B includes curved tip edge section 39B merging with curved tip edge section 39A to form the rounded distal end, an inwardly curved forward intermediate edge section 41B joining tip edge section 39B with a straight rearward intermediate edge section 42B extending proximally from forward intermediate edge section 41B parallel or substantially parallel with the middle member longitudinal axis, and a straight rearward edge section 43B extending inwardly in the direction of the middle member longitudinal axis from the rearward intermediate edge section 42B to the middle member body. As shown in FIG. 1, the walls defining the tip, forward intermediate, rearward intermediate and rearward sections are of uniform or substantially uniform thickness to define a hollow interior for the jaws communicating with the lumen or hollow interior of the middle member body. As shown in FIG. 5, jaws 30 are normally disposed in an open position wherein inner opposed surfaces 44 of the tip section walls are separated from one another by a variable size space, opening or passage 45 communicating with the hollow interior of the jaws, the tip sections 33 defining a distal end for the instrument body. Jaws 30 are movable inwardly toward one another, i.e. toward a longitudinal axis of the ligating instrument, from the normally open position to a closed position by engagement of the outer member distal end 24 with the walls forming rearward sections 36 as shown in FIGS. 1 and 2. In the closed position, the tip sections 33 are disposed closer to one another and, therefore, closer to the instrument axis, than they are in the open position such that the size of passage 45 between inner surfaces 44, in a direction transverse or perpendicular to the instrument longitudinal axis, is smaller than the size of the passage in the open position. Jaws 30 are maintained in the closed position due to constraint by the outer member; and, when the outer member is moved proximally relative to the middle member and/or the middle member is moved distally relative to the outer member, the jaws 30 automatically return to the open position. The jaws can be designed in many various ways to be normally disposed in the open position and to be moved to and maintained in the closed position or the jaw member can be normally disposed in the closed position and moved to and maintained in the open position. The jaw member can be of the type disclosed in applicant's prior applications Ser. No. 08/366,285, filed Dec. 29, 1994, Ser. No. 08/377,723, filed Jan. 25, 1995 and Ser. No. 08/401,002, filed Mar. 9, 1995, the disclosures of which are incorporated herein by reference. In the case of instrument 10, the jaws 30 are made of resilient, flexible or spring materials to be flexible and/or spring biased in the open position. In addition or alternative to engagement of rearward sections 36 by outer member 16, the instrument 10 can be designed in many other ways to maintain the jaws in the closed position and to permit selective opening of the jaws. It should be appreciated that the jaws do not have to be normally disposed in the open position; rather, the jaws can be normally disposed in the closed position and mechanically moved to the open position during operation of the ligating instrument.

The cutter 20 comprises a tubular or hollow body having a proximal end connected to end wall 26, a distal end carrying or formed as opposed, longitudinally extending cutting fingers 46 and a lumen, internal passage or channel aligned with aperture 27. The cutter 20 preferably has an external diameter or cross-sectional size to be closely received within the middle member 18 while allowing the middle member and cutter to move longitudinally relative to one another. The cutting fingers 46 carry or are formed as inwardly curving or angled cutting blades 48 and are normally disposed in a non-cutting position wherein the cutting blades 48 are separated or spaced from one another to define a space or passage therebetween allowing ligature material of the ligature supply 14 to pass between the cutting blades 46 as shown in FIG. 1. The cutting fingers 46 are movable inwardly toward one another in the direction of a longitudinal axis of cutter 20 from the non-cutting position to an operational or cutting position wherein the cutting blades 48 are disposed closer to one another to cut the ligature material therebetween. The cutting fingers or blades can be designed in many various ways to be normally disposed in the non-cutting position and to be moved to the cutting position. In the case of instrument 10, the cutting fingers 46 are made of resilient, flexible or spring materials to be flexible and/or spring biased in the non-cutting position and to be moved to the cutting position by engagement of the cutting fingers with the inner surfaces of the walls forming the angled forward intermediate sections 34 of jaws 30 as explained further below. Various cutters suitable for use in the ligating instruments according to the present invention are disclosed in applicant's prior applications Ser. No. 08/195,491, filed Feb. 14, 1994, and Ser. No. 07/930,320, filed Aug. 17, 1992, and now U.S. Pat. No. 5,334,199, the disclosures of which are incorporated herein by reference.

Handle 22 includes a pair of hand grips 49A and 49B pivotally connected to one another at a joint 50 including a pin passing through the hand grips. An upper end of hand grip 49A is pivotally connected to a retention block 51 having a recess therein for receiving flange 32 of middle member 18, the hand grip 49A being connected to the retention block 51 at a joint 52 including a pin passing through the retention block and the hand grip. As best shown in FIGS. 1 and 6, longitudinal slots 53 are formed in outer member 16, and the middle member flange 32 passes through and is movable along the slots 53. The upper end of hand grip 49B is pivotally connected to a retention block 54 having a recess therein for receiving flange 28 of outer member 16, the hand grip 49B being connected to the retention block 54 at a joint 55 including a pin passing through the retention block 54 and the hand grip 49B. A curved spring 56 is connected between the upper ends of hand grips 49A and 49B and maintains the handle 22 in a rest position as shown in FIG. 1 wherein the upper ends of the hand grips 49A and 49B are spaced from one another. Lower ends of hand grips 49A and 49B are configured as circular or substantially circular finger rings 57A and 57B, respectively, by means of which the handle may be grasped to manipulate and operate the instrument. Handle 22 can be manually squeezed or compressed via finger rings 57A and 57B causing the upper ends of hand grips 49A and 49B to be moved from the rest position toward one another, or the handle 22 can be manually spread causing the upper ends of hand grips 49A and 49B to be moved from the rest position further away from one another. In each case, removal of the manual squeezing or spreading force results in the handle being returned to the rest position by the restoring force of spring 56. Although both hand grips are pivotable in handle 22, it should be appreciated that one hand grip can be fixed, such as by being rigidly connected to pin 50, while the other hand grip can be pivotable. Handle 22 can include a locking mechanism for locking the handle in various incremental squeezed or spread positions. In the case of instrument 10, finger ring 57B is provided with a protrusion 58B carrying a plurality of locking teeth for engaging corresponding locking structure carried by a protrusion 58A of finger ring 57A for locking handle 22 in various incremental squeezed or spread positions. An insulated connector 59 is connected with an electrically conductive element of the instrument 10 for performing unipolar or bipolar electric coagulation. For example, the connector 59 enters retention block 51 at upper longitudinal slot 53 and is connected with the middle member 18, which is made of electrically conductive material allowing jaws 30 to be used as conductive elements.

As shown in FIGS. 1 and 7, multiple loop ligature supply 14 comprises a plurality of serially arranged, pre-formed, variable size or contractible ligature loops 60 connected to one another and carried by or wound on a spool or wheel 62 defining an operating member. Each ligature loop is formed by two juxtaposed lengths of filamentous ligature material 64A and 64B connected to one another by spaced knotting elements 66 and 68. Lengths of ligature material 64A and 64B are each formed by a continuous length of ligature material passing through the knotting elements and can be made of bioabsorbable or non-bioabsorbable, stretchable or non-stretchable, hollow or solid filamentous ligature material. Where the ligature material is hollow, holes can be formed in the ligature material for the delivery of medicaments or other substances therethrough. The combined cross-sectional size of the lengths of ligature material 64A and 64B is small enough to allow the lengths of ligature material, when juxtaposed or arranged side-by-side, to slide through passage 45 when the jaws 30 are in the closed position. Knotting elements 66 are alternately arranged with knotting elements 68 along the two lengths of ligature material such that each knotting element 66 is disposed between two knotting elements 68, except for the first knotting element 66' which has free ends or tails 65A and 65B of the lengths of ligature material, respectively, extending distally therefrom. Knotting elements 66 are fixedly or immovably carried by, attached to or secured to the two lengths of ligature material such that segments of the lengths of ligature material attached to the knotting elements 66 cannot move relative to the knotting elements 66. Each knotting element 66 defines a distal end of a ligature loop 60. Knotting elements 68 are movement permitting knotting elements and are carried by, attached to or secured to the lengths of ligature material in a manner permitting movement of the lengths of ligature material relative to the knotting elements 68 to reduce the size of loops 66. Knotting elements 68 are movable longitudinally along the two lengths of ligature material to allow the ligature loops to be reduced in size, and each knotting element 68 defines a proximal end of a ligature loop 60. Accordingly, as shown in FIG. 7, the first ligature loop 60' is defined by the first movement permitting knotting element 68', a portion 64A' of the length of ligature material 64A extending distally from the first movement permitting knotting element 68' to the first fixed knotting element 66', the first fixed knotting element 66', and a portion 64B' of the length of ligature material 64B extending proximally from the first fixed knotting element 66' back to the first movement permitting knotting element 68'. The ligature loop 60' is closed or tightened by pulling the two lengths of ligature material 64A and 64B proximally as the movement permitting knotting element 68' is moved distally toward the fixed knotting element 66' or is held in place.

As best shown in FIG. 8, each knotting element 66 includes a spherical body made of a medical grade bioabsorbable or non-bioabsorbable material and having one or more attachment sites for fixedly receiving or securing first segments of the lengths of ligature material 64A and 64B, respectively. The attachment sites for knotting element 66 include juxtaposed, adjacent passages 69A and 69B extending entirely through the body of the knotting element for receiving first segments of the lengths of ligature material 64A and 64B, respectively. The first segments are immovably held in passages 69A and 69B with a tight friction fit; however, the knotting element 66 can itself alternatively or additionally include structure, such as locking protrusions in passages 69A and 69B, for fixedly securing or gripping the lengths of ligature material or the knotting element can be held in place with the use of adhesives or can be bonded to the lengths of ligature material, for example. The spherical body of knotting element 66 has an external configuration, diameter or cross-sectional size to permit passage of the knotting element 66 between the inner surfaces 44 of jaws 30 when the jaws are in the open position and to prevent passage of the knotting element between the inner surfaces when the jaws are in the closed position, the cross-sectional size of the knotting element 66 being greater than the combined cross-sectional size of the lengths of ligature material 64A and 64B. However, it should be appreciated that the knotting element 66 can have a configuration or cross-sectional size permitting passage of the knotting element between the jaws in the closed position and that the knotting element 66 does not have to be a separate member or component. For example, the knotting element 66 can be formed by adhesively securing the lengths of ligature material to one another. The knotting elements 66 can have various configurations, including various clip configurations, and can be designed in many various ways to fixedly receive or be attached to the lengths of ligature material as disclosed in applicant's prior applications Ser. No. 08/366,285, Ser. No. 08/377,723, and Ser. No. 08/401,002 incorporated herein by reference.

As shown in FIG. 9, each knotting element 68 includes a substantially spherical body made of medical grade bioabsorbable or non-bioabsorbable, plastically deformable or malleable material and having one or more attachment sites for receiving segments of the lengths of ligature material 64A and 64B, respectively. The attachment sites for knotting element 68 include juxtaposed, adjacent passages 70A and 70B extending entirely through the body of the knotting element and communicating with a mouth, space, recess or notch 71 between a pair of opposed legs or jaws 72 carrying opposed angularly oriented surfaces 74. The spherical body of knotting element 68 has an external configuration, diameter or cross-sectional size to permit passage of the knotting element 68 between the inner surfaces 44 of jaws 30 when the jaws are open and to prevent passage of the knotting element between the inner surfaces when the jaws are closed, the cross-sectional size of the knotting element 68 being greater than the combined cross-sectional size of the lengths of ligature material 64A and 64B. The knotting elements 68 are normally disposed in an open position as shown in FIG. 9, with the lengths of ligature material 64A and 64B longitudinally movable along passages 70A and 70B, respectively. In order to secure a ligature, the configuration of the movement permitting knotting element of the ligature loop forming the ligature is changed to fix the movement permitting knotting element to the ligature material to prevent expansion of the ligature loop as explained further below. Knotting elements 68 are plastically deformable, such as in a lead-type deformation manner, to be moved from the open position to a closed position wherein legs 72 are brought toward one another to clamp the legs together to grip the segments of the lengths of ligature material disposed in passages 70A and 70B, the passages 70A and 70B being reduced in size, collapsed or flattened in the closed position as shown in FIG. 10. The knotting elements 68 can have various configurations, including various standard or conventional clip configurations, and can be designed in many various ways, including with or without mouth 71, to movably receive or be attached to the lengths of ligature material and to be plastically deformable, changeable in configuration or spring loaded to grip, fix or immovably secure the lengths of ligature material as disclosed in the aforementioned prior application Ser. No. 08/366,285, Ser. No. 08/377,723, and Ser. No. 08/401,002 incorporated herein by reference.

As shown in FIGS. 6 and 7, spool 62 includes a pair of circular end flanges 76 and a cylindrical shaft 77, shown in FIG. 1, extending between the end flanges and around which the lengths of ligature material 64A and 64B carrying knotting elements 66 and 68 are wound. In order to mount the ligature supply 14 to the instrument body 12, a central bore 78 is formed in shaft 77 and end flanges 76 for receiving a pin 79 passing through a pair of flat mounting bars 80 extending proximally from the outer member 16 to terminate at rounded ends. Holes are formed in mounting bars 80 adjacent the rounded ends with the holes being aligned with one another and with bore 78 for receiving pin 79. Pin 79 includes a shaft or body and an enlarged head removably attached to the shaft or body, such as via a threaded connection, to allow the pin to be withdrawn from bars 80 and spool 62 for removal and/or replacement of the ligature supply. The mounting bars 80 can be made flexible to flex outwardly of the outer member 16 to facilitate mounting, removal and/or replacement of the ligature supply.

Ligating instrument 10 includes a rotational control mechanism 82 for controlling the direction of rotation of spool 62 when the ligature supply 14 is coupled with the instrument body 12. The rotational control mechanism 82, as shown in FIGS. 6, 11 and 12, includes a two-way ratchet mechanism comprising a wheel 83 disposed between one of the end flanges 76 and the corresponding mounting bar 80 and a pawl member 84 mounted on the corresponding mounting bar 80. Wheel 83 is of uniform minimum thickness for being disposed between the one end flange 76 and the corresponding mounting bar 80 and has a central hole therein for passage therethrough by the shaft or body of pin 79 such that the wheel 83 is carried by and rotates with the spool 62. A plurality of teeth 85 are formed along the circumference of wheel 83. Pawl member 84 has a Y-shaped configuration and includes a flat finger plate or base 86 and a pair of symmetrical arms 87 extending angularly outwardly in opposite directions from finger plate 86 to terminate at pawls 88 which extend longitudinally from arms 87 in the same direction as plate 86. Plate 86 is of uniform or substantially uniform thickness and includes a straight side edge along the outer surface of bar 80 and a curved side edge opposed thereto. Pawls 88 extend laterally in the direction of spool 62 to be aligned longitudinally with teeth 85 and are flexible or resilient to be capable of bending or flexing in a direction outwardly from arms 87. Pawl member 84 is pivotally mounted on bar 80 adjacent wheel 83, such as by a pin 89 passing through pawl member 84 at the junction of arms 87 with plate 86 and passing through bar 80. Pawl member 84 is normally disposed in a neutral or unlocked position wherein neither pawl 88 is engaged with a tooth 85 as shown in FIG. 11, and the pawl member 84 can be rotationally biased to the neutral position, such as by one or more torsion springs (not shown) disposed around pin 89 and connected between bar 80 and pawl member 84. In the neutral position, spool 62 can be freely rotated in either the clockwise or counterclockwise directions without locking of the spool in the position to which it is rotated. Pawl member 84 is manually rotatable or pivotable about pin 89 via finger plate 86 to move the pawl member 84 from the neutral position to either one of two locked positions wherein one of the pawls 88 is engaged with a tooth 85. A pair of nubs or protrusions 90 are provided on the outer surface of mounting bar 80 on each side of finger plate 86 in the neutral position for engaging the finger plate to thusly lock the pawl member in the locked positions, respectively. For example, FIG. 12 illustrates pawl member 84 rotated in a clockwise direction about pin 89 from the neutral position to a first locked position wherein finger plate 86 is held between upper nubs 90 and upper pawl 88 is in engagement with a tooth 85. In the first locked position, rotation of spool 62 in a clockwise direction to wind the ligature material thereon is permitted due to upper pawl 88 being bent or flexed outwardly by teeth 85 while rotation of spool 62 in a counterclockwise direction is prevented since upper pawl 88 does not bend or flex inwardly from arm 87 and the finger plate is held between the upper nubs 90. The pawl member 84 can be returned to the neutral position under the restoring force of the torsion spring when the finger plate 86 is manually disengaged from the upper nubs 90, and the inner upper nub 90 can be flexible or resilient or be configured to permit movement of the finger plate therepast. The pawl member 84 is movable from the neutral position to the second locked position by rotating the pawl member 84, via finger plate 86, in a counterclockwise direction about pin 89 causing the lower pawl 88 to engage a tooth 85 and the finger plate 86 to be held between the lower nubs 90. In the second locked position, the spool 62 will be permitted to rotate in a counterclockwise direction to unwind the ligature material therefrom due to the lower pawl being bent or flexed outwardly by teeth 85 while rotation of the spool in a clockwise direction will be prevented since the lower pawl does not bend inwardly and the finger plate is held between the lower nubs 90. Upon disengagement of the finger plate 86 with the lower nubs 90, the pawl member will be returned to the neutral position, and the inner lower nub can be flexible or resilient or be configured to permit movement of the finger plate therepast. Accordingly, in both the first and second locked positions, controlled incremental rotation of spool 62 in one direction is possible while rotation in the opposite direction is prevented, and the spool will be locked in place by teeth 85 after a desired increment of rotation. It should be appreciated that the instrument 10 can include various other types of rotational control mechanisms, including other ratchet mechanisms, in addition to the two-way ratchet mechanism shown.

The instrument body 12 will normally be supplied as shown in FIG. 1 with the middle member 18 concentrically disposed in outer member 16 and inner member or cutter 20 concentrically disposed in middle member 18. Handle 22 will be in the rest position to position the outer, middle and inner members such that jaws 30 protrude distally from the outer member and are maintained by the outer member in the closed position due to engagement of the outer member distal end 24 with the walls defining the rearward sections 36 of the jaws. Cutting fingers 46 will be disposed in the hollow interior of the jaws in the non-cutting position with cutting blades 48 positioned proximally of the angled inner surfaces of the walls defining forward intermediate sections 34. The ligature supply 14 will normally be supplied with the lengths of ligature material 64A and 64B, including the ligature loops 60 formed thereby, wound on spool 62.

Ligating instrument 10 can be supplied assembled with the ligature supply 14 coupled with the instrument body 12 with spool 62 rotatably mounted on bars 80, or the ligating instrument can be supplied unassembled with the ligature supply 14 not coupled with the instrument body 12. Where the ligating instrument 10 is supplied assembled as shown in FIG. 1, the lengths of ligature material will be partially unwound from the spool to extend through aperture 27 to be housed or received in the instrument body. The lengths of ligature material will extend through cutter 20 and through passage 45 between the internal surfaces 44 of the jaw tip sections 33 to position the first fixed knotting element 66' externally of the jaws. The first fixed knotting element 66' cannot pass proximally through passage 45 with the jaws in the closed position and thusly will be held externally of the jaws with tails 65A and 65B extending distally from the knotting element. Although the first fixed knotting element 66' is illustrated in FIG. 1 as being positioned externally adjacent the jaw tip sections 33, it should be appreciated that the knotting element 66' can be positioned further distally of the jaw tip sections 33. There can be some slack in the lengths of ligature material extending through the instrument body to facilitate proximal movement of the outer member to open jaws 30 during operation. It should be appreciated that no knotting element need be disposed externally of the jaws when the instrument is supplied for use and that no parts of the ligature supply need protrude beyond the jaws to facilitate introduction through an endoscopic portal without snagging or catching. For example, tails 65A and 65B can extend through passage 45 to protrude externally from the jaws without protrusion of the first knotting element 66' therewith, or both the tails 65A and 65B and the first knotting element 66' can be disposed entirely within the instrument body. Where instrument 10 is supplied unassembled, the ligature supply 14 is coupled with the instrument body 12 prior to use by mounting spool 62 on bars 80 via removable pin 79 and feeding the lengths of ligature material 64A and 64B through aperture 27. Where the instrument is supplied assembled or is supplied unassembled and is assembled prior to use and the tails 65A and 65B and/or the first fixed knotting element 66' are disposed within the instrument body, the first fixed knotting element 66' and/or the tails 65A and 65B can be positioned externally of the jaws by spreading handle 22 via finger rings 57A and 57B to move the middle member 18 distally and/or the outer member 16 proximally relative to one another as permitted by slot 53. In the case of instrument 10, the outer member and cutter move slightly proximally and the middle member moves slightly distally in response to spreading operation of handle 22 causing jaws 30 to move to the open position due to release of the jaw rearward sections 36 from constraint by the outer member distal end 24. However, where hand grip 49A is fixed, such as by being rigidly connected to pin 50, and hand grip 49B is pivotable about pin 50, the outer member and cutter will move proximally relative to the middle member, which can remain in place, when the handle is spread by moving finger ring 57B away from finger ring 57A. It should be appreciated that protrusions 58A and 58B can be designed for locking interengagement when the handle is spread to lock the handle in the position corresponding to the open position for the jaws. Where so designed, the handle can be returned to the rest position by spring 56 when a manual squeezing force is applied to the handle sufficient to overcome the locking interengagement of the protrusions. With the jaws 30 in the open position, the ligature supply can be grasped, such as by grasping tails 65A and 65B and/or the first fixed knotting element 66' with a grasper or forceps instrument inserted between the open jaws. The grasper is then used to pull or move the ligature material distally through passage 45 until the first fixed knotting element 66' and/or the tails 65A and 65B are positioned externally of the jaws 30. If desired, some slack can remain in the lengths of ligature material extending through the instrument body. The pawl member 84 can be in the neutral position or in the second locked position permitting counterclockwise rotation of spool 62 and, therefore, unwinding of the ligature material. Upon release of handle 22 from the spread position, the handle will be returned to the rest position by spring 56, and the jaws 30 will be moved to the closed position due to constraint by outer member 16.

Figure 13:
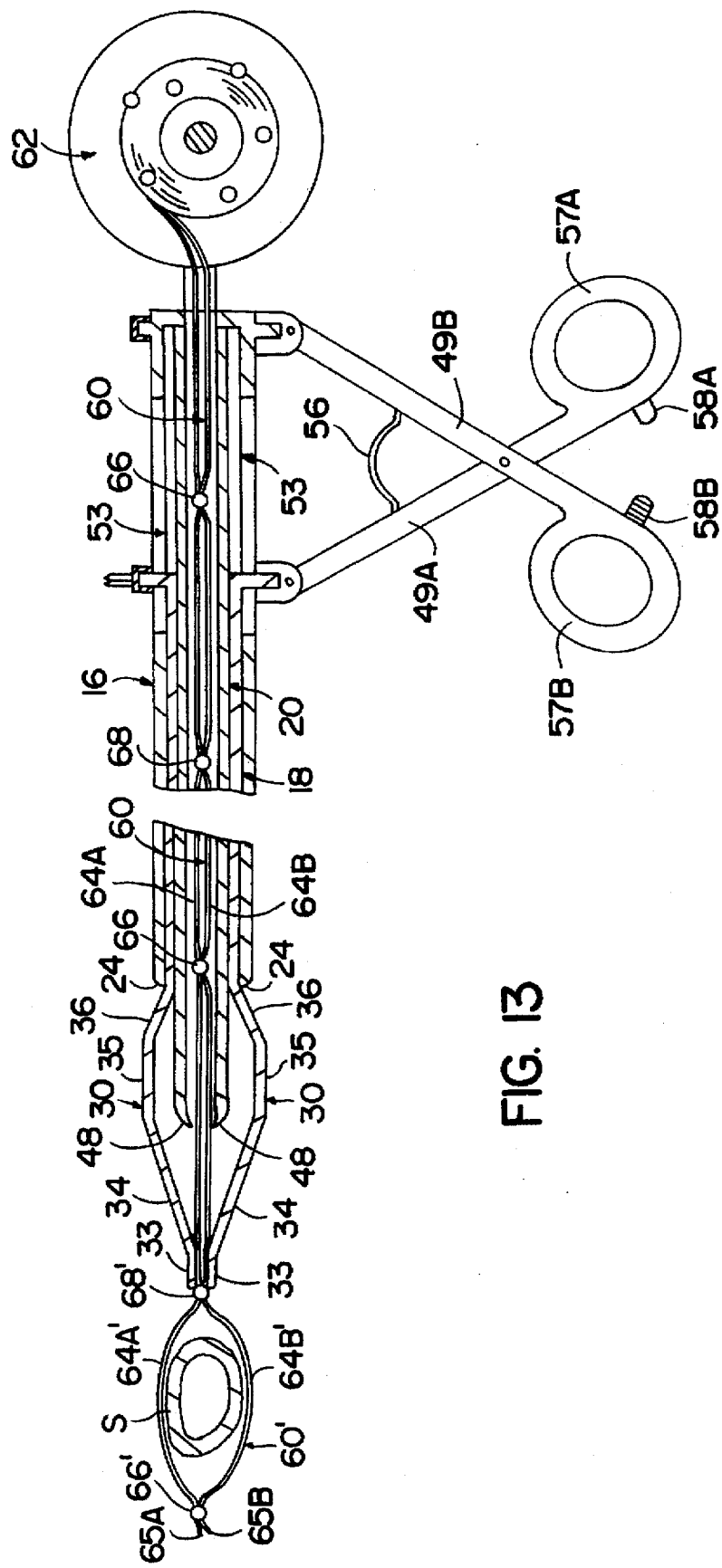
FIG. 13 is a broken side view, partly in section, of the ligating instrument showing the first ligature loop of the multiple loop ligature supply disposed externally of the jaws and positioned around an anatomical structure to be ligated.

In use, a distal end of the ligating instrument 10 is introduced at an internal operative site with the jaws 30 in the closed position and with the first knotting element 66' and/or tails 65A and 65B disposed externally of jaws 30 or with no parts of the ligature supply disposed externally of the jaws. In endoscopic procedures, the ligating instrument can be introduced at the operative site through an endoscopic portal including a structural sleeve or channel such as a portal or trocar sleeve or a small size natural or prepared anatomical opening establishing communication with the internal operative site from externally of the body. Handle 22, which is held with one hand externally of the body, is used to manipulate the ligating instrument to position the distal end thereof within the body. To deploy the first ligature loop 60', handle 22 is spread to open jaws 30 as described above allowing the ligature supply to be moved or pulled distally through passage 45, such as with a grasper introduced through a second endoscopic portal, until the first ligature loop 60' is withdrawn from the instrument body and is disposed externally of the jaws 30 as shown in FIG. 13. The pawl member 84 can be in the neutral position or in the second locked position permitting unwinding of the ligature material from the spool. Depending on what part, if any, of the ligature supply is disposed externally of the jaws when the instrument is introduced in the body, the grasper can be used to grasp the knotting element 66', the tails 65A and 65B or some other part of the ligature supply externally of or between the open jaws. Once the first loop 60', including the first movement permitting knotting element 68', is disposed externally of the jaws 30 as permitted by movement of knotting element 68' through passage 45 when the jaws are in the open position, handle 22 is moved to the rest position causing the jaws to move to the closed position. Although the movement permitting knotting element 68' is shown in FIG. 13 in abutment with the jaw tip sections 33, it should be appreciated that the knotting element 68' can be spaced distally from the jaws depending on procedural use. The first loop 60' will be held externally of the jaws since the first movement permitting knotting element 68' cannot enter or pass proximally through passage 45 once the jaws are in the closed position. It should be appreciated that, depending on procedural use, the first ligature loop can be deployed prior to introduction of the instrument at the operative site as may be particularly desirable in open procedures.

Figure 14:
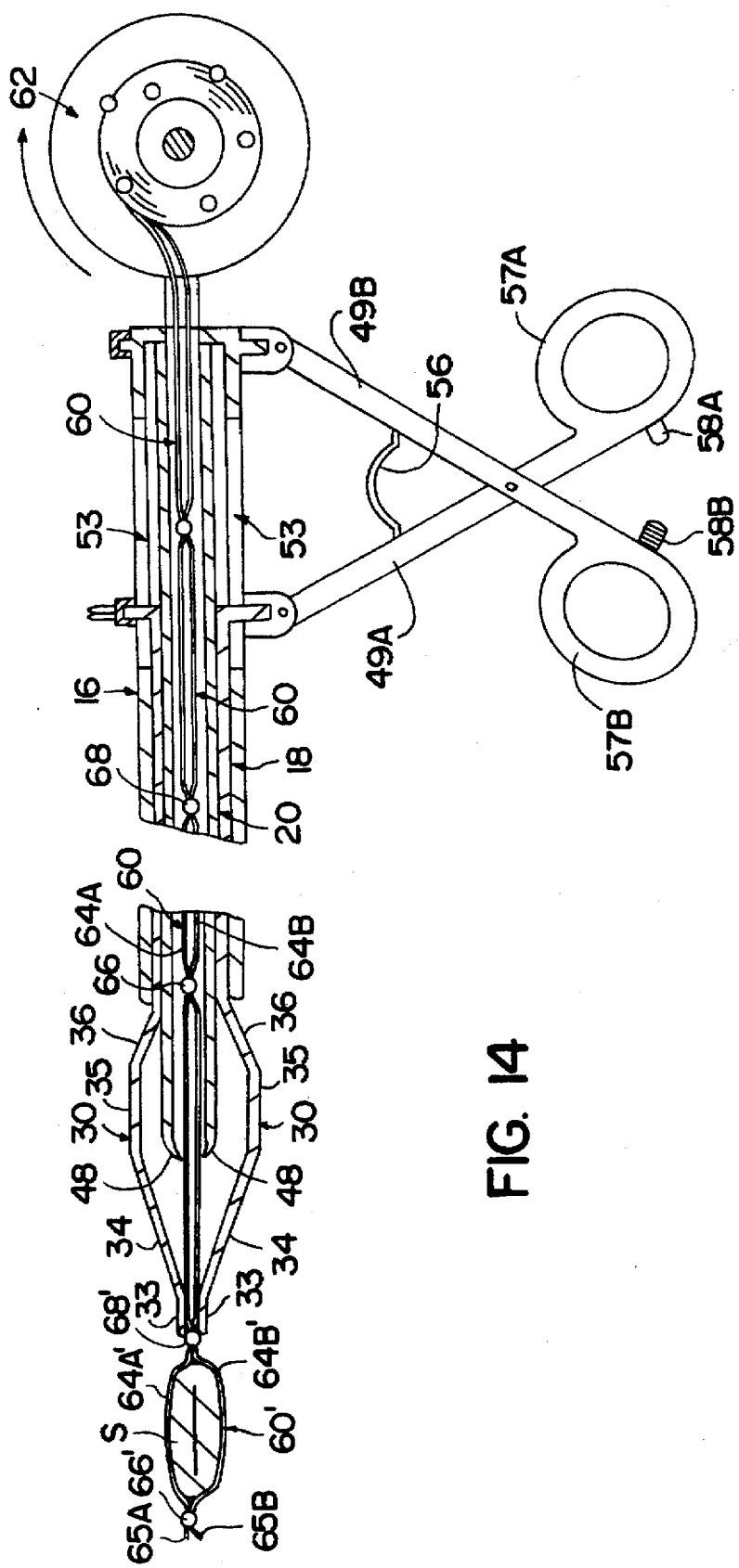
FIG. 14 is a broken side view, partly in section, of the ligating instrument showing the first ligature loop tightened around the anatomical structure to form a ligature.

To utilize the ligating instrument 10 to form a ligature in anatomical tissue including anatomical tissue structure, anatomical organ structure or any other anatomical part which it is desirable or necessary to ligate, tie or occlude, the distal end of the instrument 10 is positioned adjacent the anatomical structure S to be ligated, and the external ligature loop 60' is positioned around the anatomical structure S as shown in FIG. 13. Once the ligature loop 60' has been positioned around the anatomical structure S, the finger plate 86 is pivoted upwardly to move the pawl member 84 to the first locked position allowing controlled, incremental clockwise rotation of spool 62. To tighten the ligature loop 60' around the anatomical structure S, spool 62 is manually rotated in the clockwise direction with the thumb of the hand grasping handle 22, the spool 62 forming an operating member for moving the ligature material proximally relative to the jaw member. Clockwise rotation of spool 62 causes the lengths of ligature material 64A and 64B to be pulled proximally and to be further wound on the spool 62 while the knotting element 68' is held adjacent the jaw tip sections 33. The entire instrument 10 is simultaneously moved distally toward the anatomical structure S such that the ligature loop 60' is tightened around the anatomical structure S without pulling or displacement thereof as shown in FIG. 14, such longitudinal distal movement of instrument 10 being permitted due to sliding movement of the lengths of ligature material 64A and 64B along passage 45.

Figure 15:
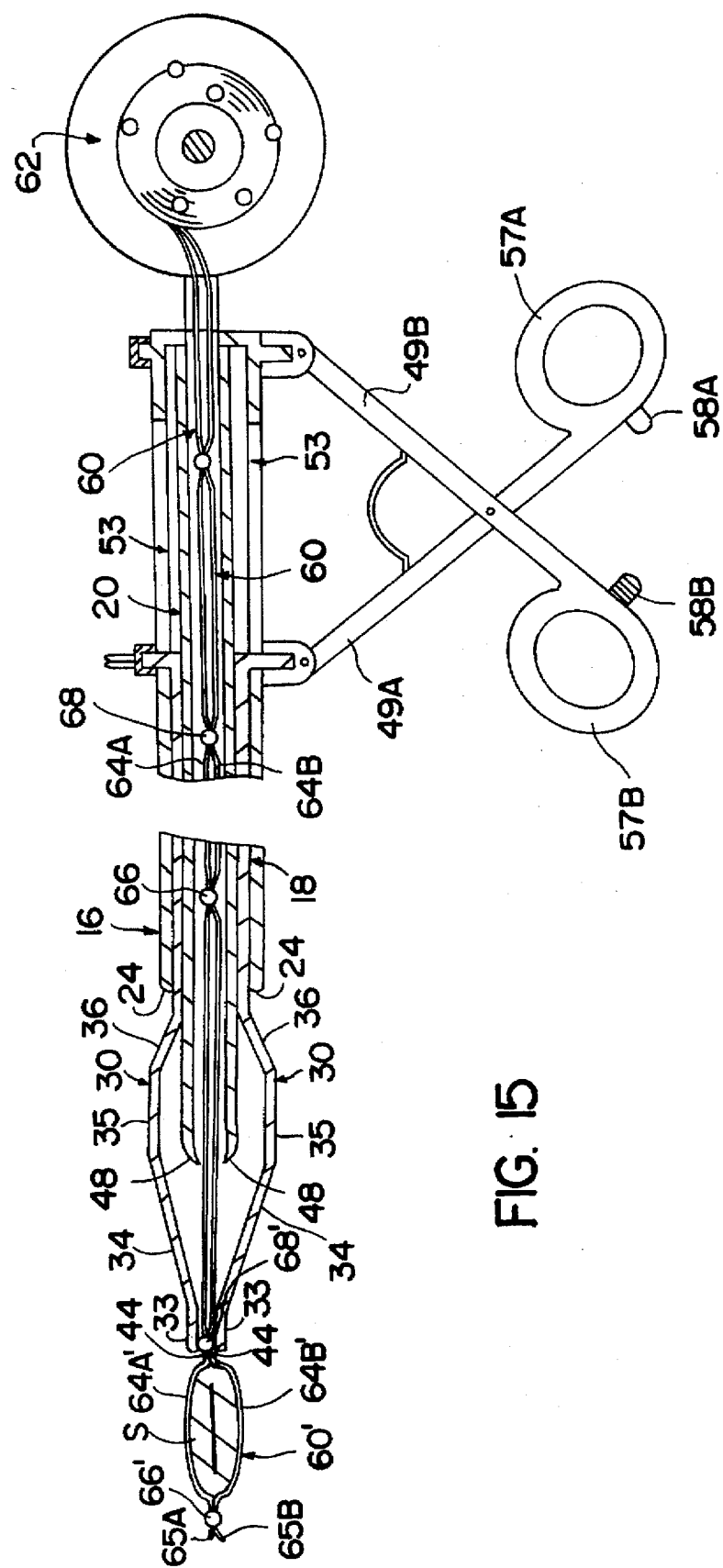
FIG. 15 is a broken side view, partly in section, of the ligating instrument showing the jaws in an open position receiving the first movement permitting knotting element therebetween.

Once the ligature loop 60' has been tightened around the anatomical structure S with a desired tension, which can be tactilely sensed or felt by the surgeon via controlled, manual incremental rotation of spool 62, handle 22 is spread to move the jaws 30 from the closed position to the open position. Prior to spreading operation of the handle 22, the pawl member is moved to the neutral position or the second locked position to allow some of the ligature material to unwind when the outer member is moved proximally or the pawl member is moved to the second locked position and the spool rotated counterclockwise to create some slack in the ligature material. With the jaws in the open position, the instrument 10 is moved slightly forward to position the first movable knotting element 68' between surfaces 44, the passage 45 being large enough to receive the knotting element 68' since the jaws are in the open position as shown in FIG. 15. Handle 22 is then squeezed causing outer member 16 and/or middle member 18 to move relative to the other to forcefully move jaws 30 toward the closed position. In instrument 10, the outer member 16 is moved slightly distally and the middle member 18 is moved slightly proximally causing the outer member distal end 24 to push inwardly on the walls forming jaw rearward sections 36. Accordingly, jaws 30 are forcefully moved toward the closed position to plastically deform, crush, crimp, crunch or compress the knotting element 68' between the jaws. The knotting element 68' will be moved to the closed position with legs 72 moved toward one another to close mouth 71 and cause the segments of the lengths of ligature material 64A and 64B to be gripped in passages 70A and 70B, which are collapsed, flattened or reduced in size. The knotting element 68' will then be fixed in place on the lengths of ligature material and will prevent the segments of ligature material in passages 70A and 70B from moving relative to the knotting element 68' to secure the thusly formed tensioned ligature. If desired, other segments of the lengths of ligature material can be positioned in mouth 71' prior to plastic deformation of knotting element 68' for additional protection or securement as explained below.

Figure 16:
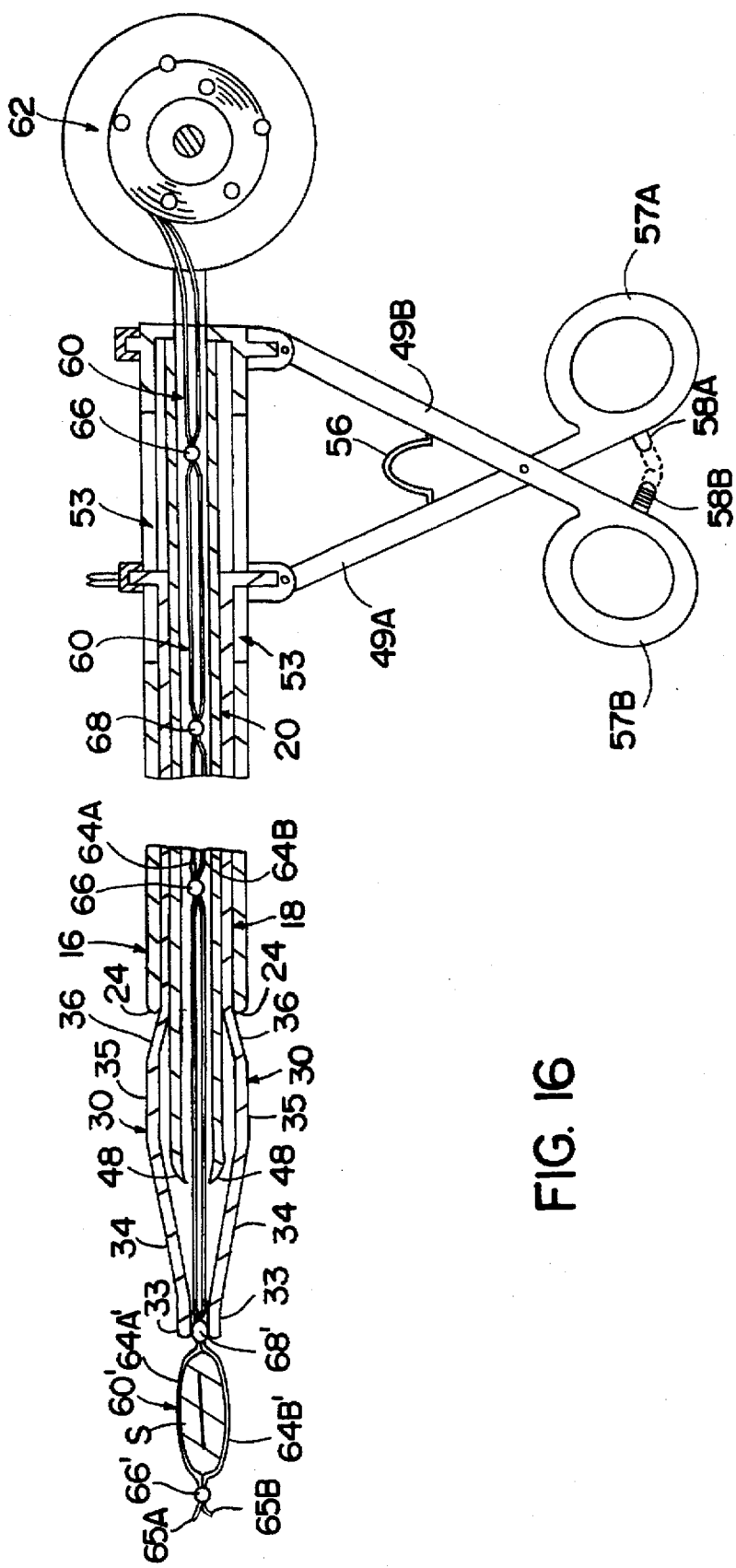
FIG. 16 is a broken side view, partly in section, of the ligating instrument showing the jaws being forcefully moved toward the closed position to plastically deform the movement permitting knotting element therebetween to secure the ligature.

When the handle 22 is squeezed to plastically deform the knotting element 68', the cutter 20 will move distally with the outer member 16. However, in instrument 10 the cutter 20 does not move far enough distally to engage the angled inner surfaces of the walls defining forward intermediate sections 34 of the jaws such that the cutter remains in the non-cutting position. As discussed above, automatic locking of the handle 22 in the closed position corresponding to plastic deformation of knotting element 68' can be obtained via cooperative interlocking engagement of protrusions 58A and 58B when the handle is squeezed, as shown in dotted lines in FIG. 16, in which case the protrusions can be disengaged when the handle is spread with a manual force sufficient to overcome the locking force of the protrusions. If necessary, the entire instrument can be moved slightly distally when the movable knotting element is plastically deformed to avoid displacement of the ligature. Where only hand grip 49B is pivotable, however, the outer member will move distally relative to the middle member such that the instrument does not have to be moved forwardly since the jaws do not move proximally away from structure S.

Figure 17:
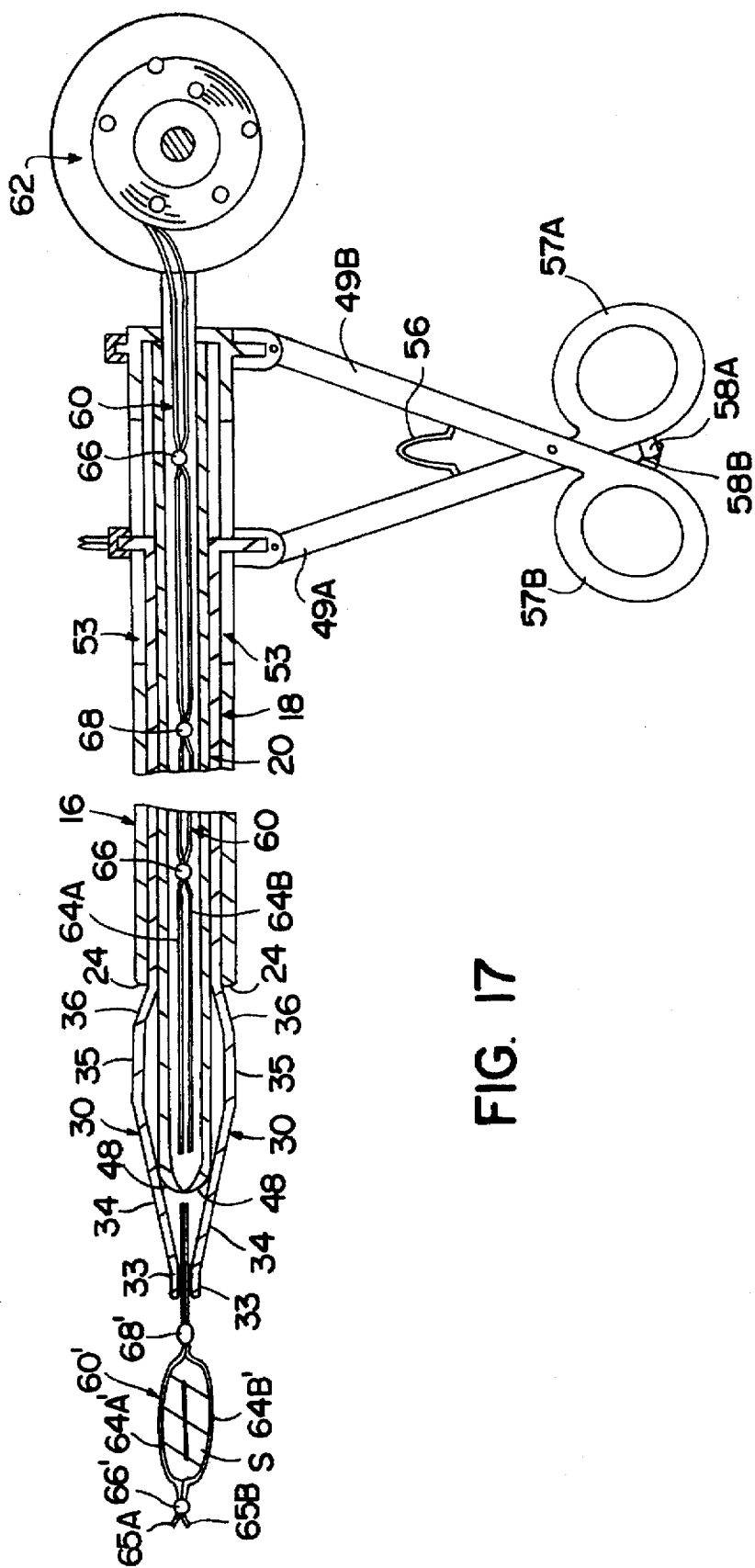
FIG. 17 is a broken side view, partly in section, of the ligating instrument showing the cutter moved to the cutting position to cut the lengths of ligature material proximally of the ligature.

Once the knotting element 68' has been fixed to the ligature material, handle 22 is spread to open jaws 30 to release the knotting element 68' and to allow the instrument 10 to be backed slightly away from the ligature. Prior to spreading the handle, the pawl member 84 can be moved to the second locked position and the spool 62 rotated counterclockwise to create some slack in the lengths of ligature material 64A and 64B, or the pawl member can be in the neutral position or the second locked position allowing the ligature material to unwind when the handle is spread and the instrument backed away from the ligature. Once the instrument 10 has been backed away from the ligature, handle 22 is squeezed to move jaws 30 to a second or further closed position wherein the cutter 20 is moved further distally to engage the angled inner surfaces of the walls defining forward intermediate sections 34 to cause the cutter to move to the cutting position wherein cutting blades 48 are moved inwardly to cut the lengths of ligature material 64A and 64B proximally of the ligature. Movement of the jaws 30 to the second closed position is permitted due to there being no knotting element between the jaws, and the handle 22, which forms an actuator for moving the cutter from the non-cutting position to the cutting position, can be automatically locked in the second closed position via interengagement of protrusions 58A and 58B as shown in FIG. 17. It should be appreciated that the cutter 20 can be designed, such as by increasing the length thereof, to engage the inner surfaces of the walls defining forward intermediate sections 34 when the handle 22 is squeezed to plastically deform the knotting element 68' such that the cutter is moved to the cutting position to cut the lengths of ligature material proximally of the ligature simultaneously with securement of the ligature.

Figure 18:
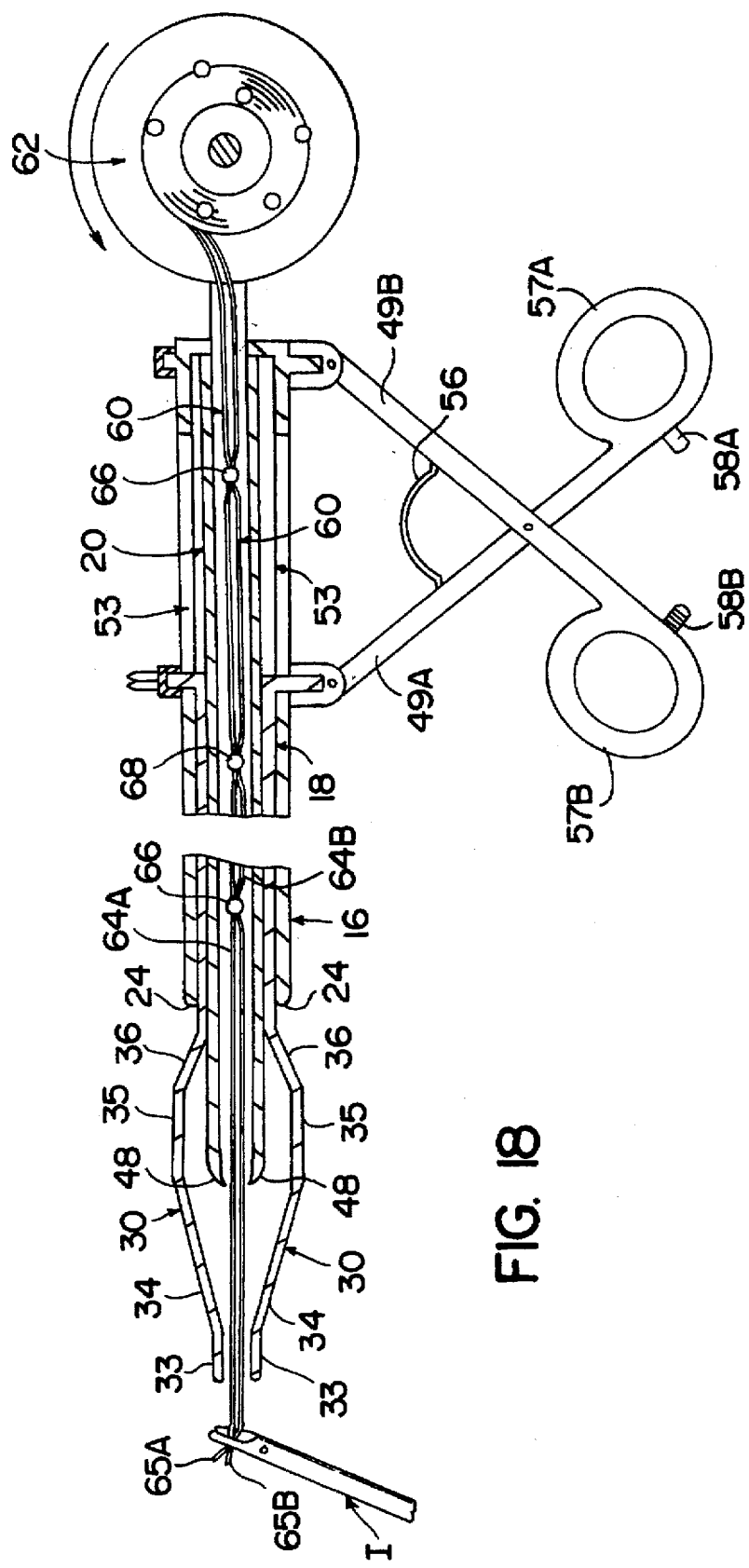
FIG. 18 is a broken side view, partly in section, of the ligating instrument showing the lengths of ligature material being pulled distally to position the next ligature loop externally of the jaws.

After the lengths of ligature material have been cut proximally of the knotting element 68', the ligature is left in place and the instrument 10 can be utilized to form another ligature. The handle 22 is spread manually with a force sufficient to overcome the locking force of protrusions 58A and 58B allowing the handle to return to the rest position. With pawl member 84 in the second locked position or in the neutral position, spool 62 can be rotated counterclockwise as shown in FIG. 18 to unwind or advance the lengths of ligature material 64A and 64B distally through the instrument body. The handle 22 is spread to open jaws 30 allowing the next two knotting elements, i.e. a fixed knotting element 66 and a movement permitting knotting element 68, forming the next ligature loop 60 to be withdrawn from the instrument body and positioned externally of the jaws 30, such as with a grasper or forceps I grasping the new free ends or tails 65A and 65B of the lengths of ligature material. It should be appreciated that the instrument can be designed with a mechanism for driving or pushing the ligature material through the instrument body. For example, the instrument body can include friction rollers or a control trigger which causes a pusher to advance a knotting element externally of the jaws. Accordingly, the ligating instrument 10 will be ready for use to form another ligature or tie without withdrawal of the instrument from the body.

It should be appreciated that use of the ligating instrument can include contacting anatomical tissue or structure with the jaws and transmitting electrical energy to the tissue to treat the tissue, such as for electrical coagulation, via the jaws and connector 59. In addition, use of the ligating instrument can include taking measurements or dimensions in the body via scale 29, such as taking measurements of organs, tissue or other anatomical structure as well as tumors and anatomical voids, cavities and spaces. For example, ligating instrument 10 can be utilized to obtain the longitudinal size or length of structure S by aligning the outer member distal end 24 with one end of structure S and noting the distance from the outer member distal end 24 to the indicia line or other point on the scale aligned with the opposite end of structure S.

Figure 19:
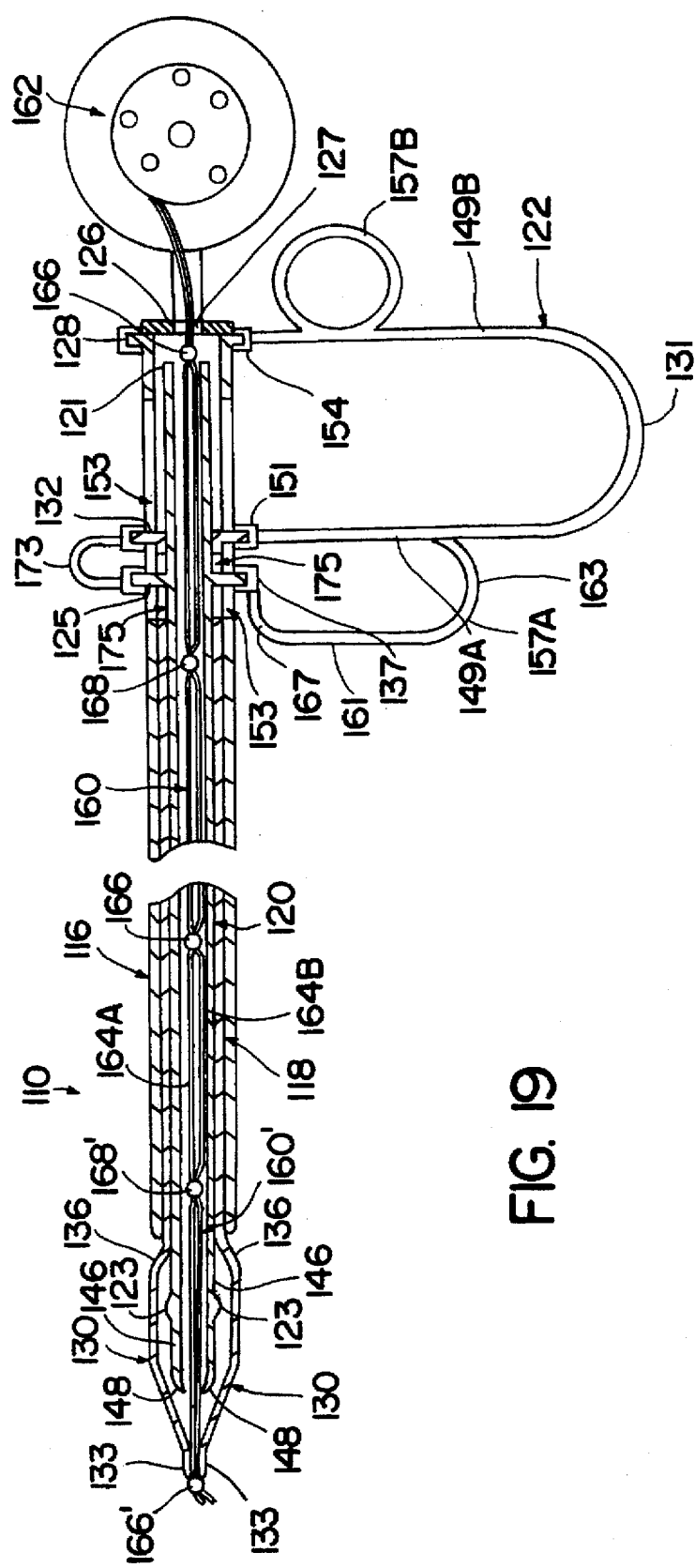
FIG. 19 is a broken side view, partly in section, of a modification of a ligating instrument according to the present invention.

A modification of a ligating instrument according to the present invention is illustrated at 110 in FIG. 19. Ligating instrument 110 is similar to ligating instrument 10 except that cutter 120 and handle 122 for ligating instrument 110 are different from cutter 20 and handle 22 for ligating instrument 10. Cutter 120 includes a tubular or hollow body terminating proximally at an open proximal end 121 aligned with aperture 127, the proximal end 121 being spaced distally of outer member end wall 126 when the outer member 116, the middle member 118 and the cutter 120 are positioned by handle 122 in the rest position. A distal end of the cutter body carries or is formed as opposed, longitudinally extending cutting fingers 146 which in turn carry or are formed as inwardly curving or angled cutting blades 148. A bump, nub or protrusion 123 is disposed on each cutting finger 146 proximally of a distal end of cutting blade 148. The cutter body is configured as or provided with a transverse or radially extending flange 125 disposed distally of the cutter proximal end 121 and coupled with handle 122 as explained below.

Handle 122 has a U-shaped configuration defining a forward handgrip 149A and a rearward handgrip 149B having a lower end connected to a lower end of the forward handgrip by a curved base 131. An upper end of handgrip 149A is connected to a retention block 151 having a recess therein for receiving flange 132 of middle member 18, the flange 132 passing through opposed slots 153 in outer member 116. An upper end of handgrip 149B is connected to a retention block 154 having a recess therein receiving flange 128 of outer member 16. Handle 122 is at least partly made of resilient, flexible or spring materials with base 131 maintaining the handle 122 in the rest position wherein the upper ends of handgrips 149A and 149B are spaced from one another as shown in FIG. 19 while allowing the upper end of handgrip 149B to be moved toward the upper end of handgrip 149A when the handle is squeezed and to be moved further away from the upper end of handgrip 149A when the handle is spread. Handgrip 149B is provided with a circular finger ring 157B. Handgrip 149A is provided with an oblong finger ring 157A opposed to finger ring 157B and connected between the handgrip 149A and a retention block 137 having a recess therein for receiving the cutter flange 125. Finger ring 157A includes a straight finger grip portion 161 connected to the forward handgrip 149A by a curved lower base portion 163 and connected to retention block 137 by a curved upper base portion 167. Finger ring 157A is made at least partly of resilient, flexible or spring materials with lower base portion 163 maintaining the finger ring 157A in a rest position wherein finger grip portion 161 is spaced distally from handgrip 149A while allowing the finger grip portion to be moved toward handgrip 149A when the finger ring 157A is squeezed or compressed with a manual squeezing force. A curved spring 173 is arranged bilaterally with finger ring 157A and is connected between the retention blocks 137 and 151 to bias the cutter 120 distally relative to the middle member 118. Spring 173 positions the cutter in a non-cutting position with bumps 123 disposed distally of the angled inner surfaces of the walls defining the jaw rearward sections 136 and with finger grip 157A in the rest position. Longitudinal slots 175 are formed in middle member 118, and the cutter flange 125 passes through and is movable along the slots 175 to allow longitudinal movement of the cutter relative to the middle member when the finger ring 157A is squeezed.

Figure 20:
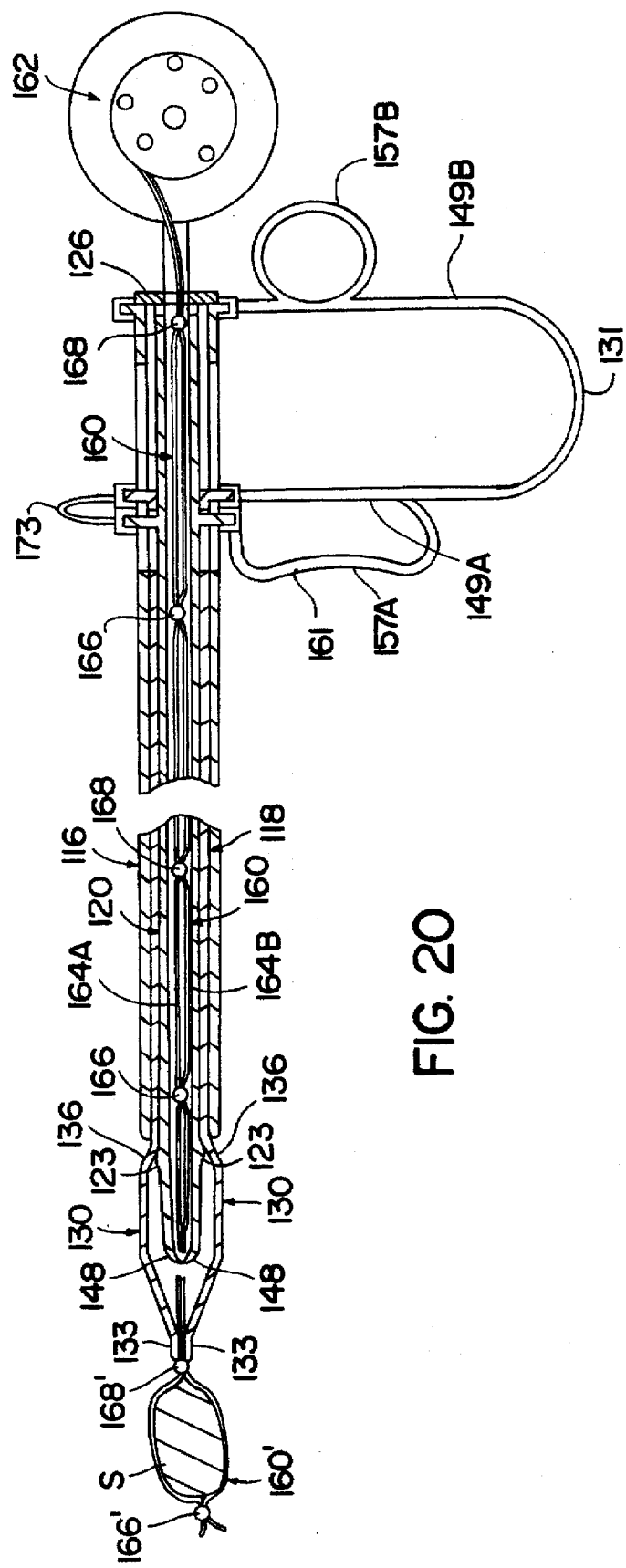
FIG. 20 is a broken side view, partly in section, showing the lengths of ligature material being cut proximally of a ligature formed with the ligating instrument of FIG. 19.

Use of ligating instrument 110 is similar to that described above in that handle 122 is spread via handgrip 149B to move the outer member 116 proximally relative to the middle member 118 to open jaws 130. By moving finger ring 157B proximally relative to handgrip 149A, handgrip 149B will move proximally to correspondingly move the outer member 116 while the handgrip 149A can remain fixed or stationary. Once the jaws 130 have been opened, the first ligature loop 160' is deployed externally of the jaws. Thereafter, handle 122 is returned to the rest position, such as via the restoring force of the spring materials of the handle. The externally deployed ligature loop 160' is then placed around anatomical structure S to be ligated as shown in FIG. 20, and the spool 162 is rotated clockwise to tighten the ligature loop 160' around the anatomical structure S with a desired tension or force. Handle 122 is then spread to open jaws 130 to receive the knotting element 168' between the internal surfaces of the jaw tip sections 133. To fix the knotting element 168' to the ligature material, handle 122 is squeezed by moving the handgrip 149B toward the handgrip 149A to move the outer member 116 distally relative to the middle member 118 while the handgrip 149A can remain essentially fixed or stationary. Accordingly, jaws 130 will be forcefully moved toward the closed position due to engagement of the jaw rearward sections 136 by the distal end of outer member 116 to compress the knotting element 168'. The instrument 110 is backed away from the ligature as shown in FIG. 20 wherein jaws 130 are positioned just proximally of the knotting element 168'; however, jaws 130 can be backed farther away from the ligature depending on procedural use. As shown in FIG. 20, finger ring 157A, which forms an actuator for moving the cutter from the non-cutting position to the cutting position, is squeezed by moving finger grip portion 161 toward handgrip 149A causing the cutter 120 to be moved proximally relative to the middle member 118. Proximal movement of cutter 120 relative to middle member 118 causes bumps 123 to engage the angled inner surfaces of the walls defining the jaw rearward sections 136 which in turn causes the cutter 120 to be moved to the cutting position with fingers 146 moved inwardly toward one another causing cutting blades 148 to cut the lengths of ligature material 164A and 164B therebetween. The cutter proximal end 121 can be designed to abut or engage the outer member end wall 126 to serve as a positive stop or abutment when the finger ring 157A is squeezed to move the cutter to the cutting position. Once the squeezing force on finger ring 157A is released, the cutter 120 will be moved distally to the non-cutting position due to the restoring force of finger ring 157A and/or spring 173.

Figure 21:
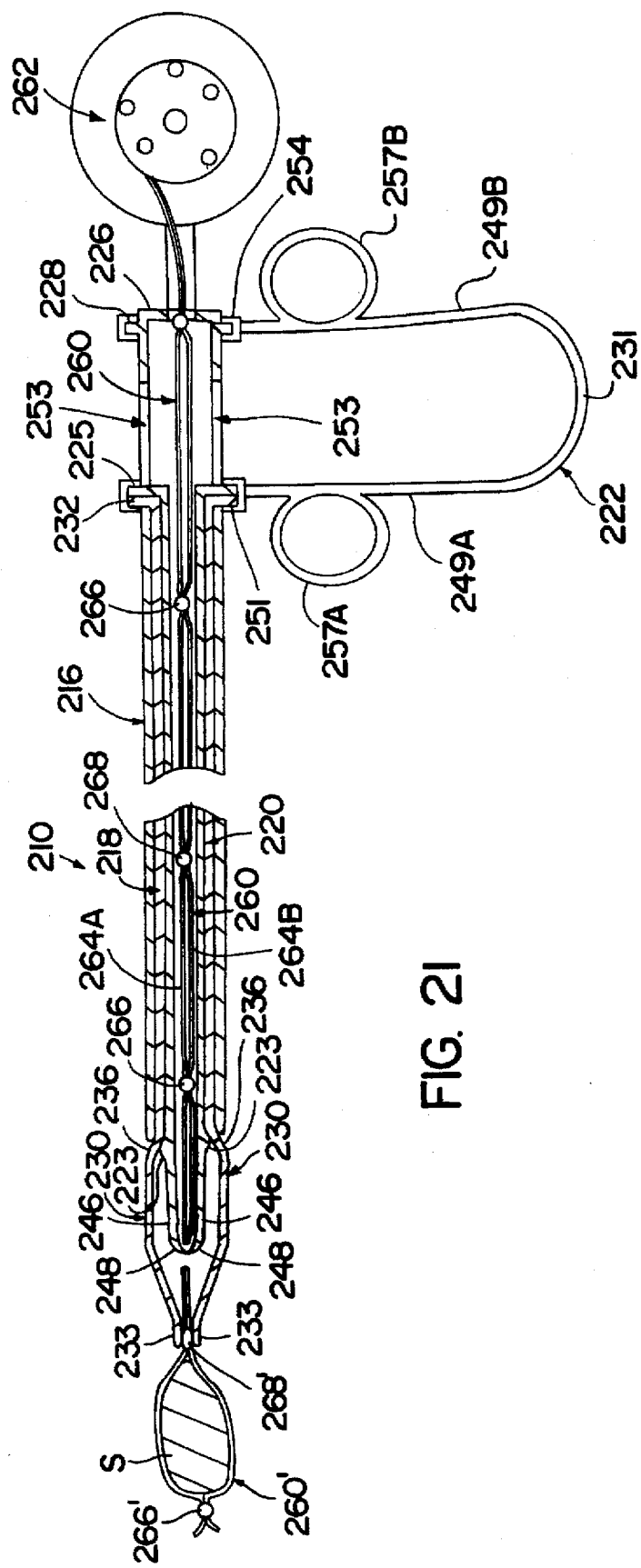
FIG. 21 is a broken side view, partly in section, of another modification of a ligating instrument according to the present invention showing the lengths of ligature material being cut proximally of a ligature simultaneously with securement of the ligature.

FIG. 21 illustrates at 210 another modification of a ligating instrument according to the present invention. Ligating instrument 210 is similar to ligating instrument 110 except that ligating instrument 210 is designed to provide cutting of the lengths of ligature material proximally of the ligature simultaneously with plastic deformation of the movement permitting knotting element. Outer member 216 for ligating instrument 210 includes a proximal flange 228 received in a recess of retention block 254 connected with rearward handgrip 249B of U-shaped handle 222. Middle member 218 terminates proximally at flange 12 received in a recess of retention block 151' connected with forward handgrip 249A. Cutter 220 extends through the open proximal end of the middle member to terminate at a flange 225, disposed proximally of flange 232, received in the recess of retention block 251 such that the middle member 218 and cutter 220 are connected to one another with flanges 225 and 232 passing through slots 253 in outer member 216. Cutter 220 has bumps 223 positioned by handle 222 in the rest position to be in contact with the inner surfaces of the walls defining the jaw rearward sections 236 with the cutter in the non-cutting position.

Use of instrument 220 is similar to that described above with the handle 222 being spread to open jaws 230 and being squeezed to forcefully move jaws 230 toward the closed position to fix the knotting element 268' to segments of the ligature material as shown in FIG. 21. Squeezing operation of handle 222, which forms an actuator for the cutter, causes the distal end of outer member 216 to push inwardly on the jaw rearward sections 236 which, due to contact with bumps 223, causes the cutting fingers 246 to be moved inwardly toward one another. Accordingly, the cutter 220 will be moved to the cutting position to cut the lengths of ligature material 264A and 264B simultaneously with securement of a ligature.

Figure 22:
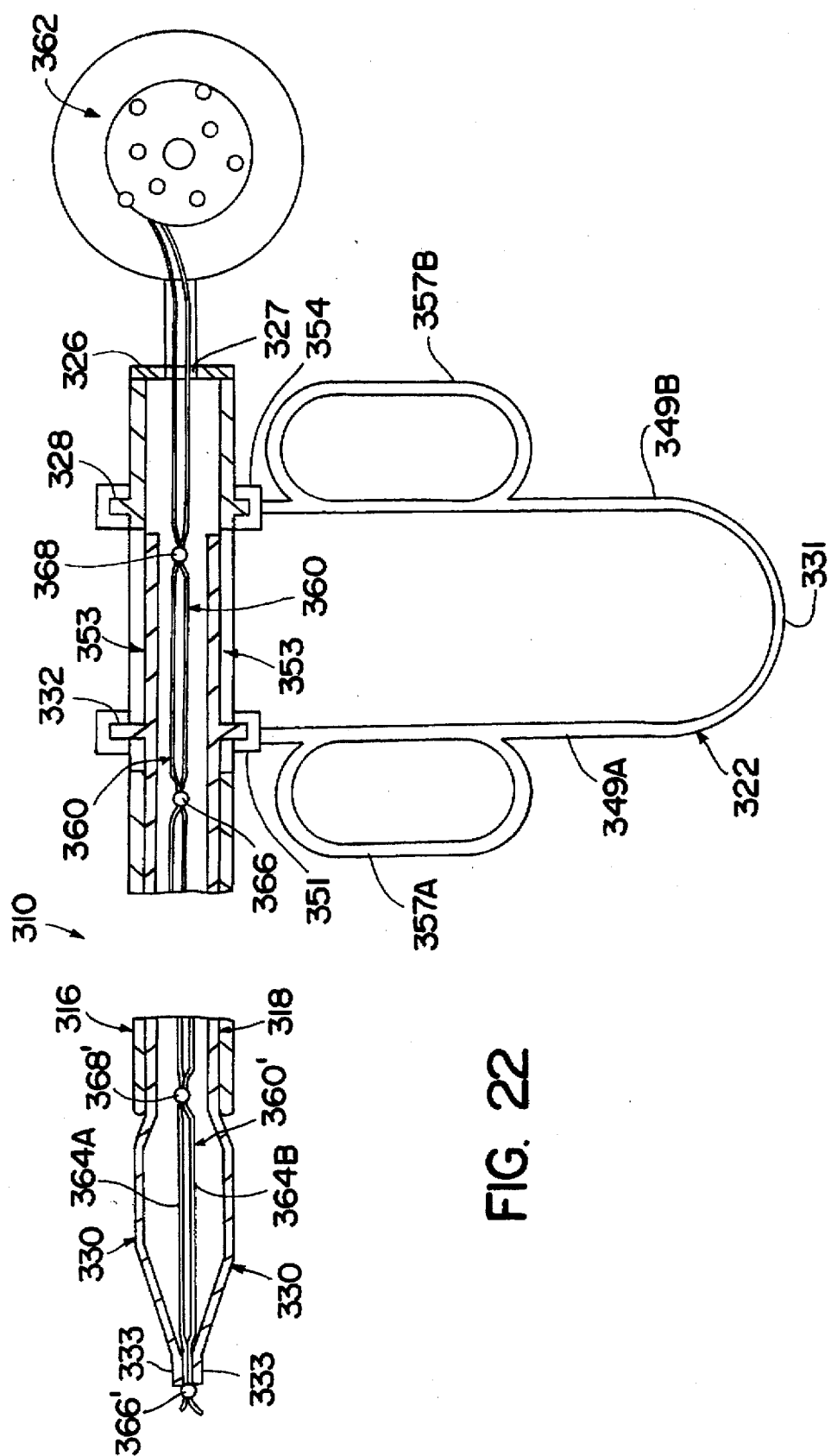
FIG. 22 is a broken side view, partly in section, of a further modification of a ligating instrument according to the present invention.

Another modification of a ligating instrument according to the present invention is illustrated at 310 in FIG. 22. Ligating instrument 310 is similar to ligating instruments 110 and 210 except that ligating instrument 310 does not include a cutter. Accordingly, the instrument body for ligating instrument 310 includes outer member 316, jaw member 318 received in outer member 316 and handle 322 mounting the outer member 316 and jaw member 318. Outer member 316 has a flange 328 disposed distally of end wall 326 and received in a recess of retention block 354 connected to rearward handgrip 349B of U-shaped handle 322. Jaw member 318 terminates proximally at a proximal end disposed in outer member 16 and has a flange 332 received in a recess of retention block 351 connected to forward handgrip 349A of handle 322. Handgrips 349A and 349B include oblong shaped finger rings 357A and 357B, respectively, facilitating manipulation of handle 322 to operate the ligating instrument 310.

Use of ligating instrument 310 is similar to that described above except that the lengths of ligature material 364A and 364B are cut proximally of a ligature with a separate cutting instrument which, in the case of endoscopic procedures, can be introduced through the same portal as the ligating instrument or through a second endoscopic portal. Accordingly, the lengths of ligature material will be cut externally of jaws 330 such that new tails or free ends of the lengths of ligature material will protrude from the Jaws 330 subsequent to cutting to be grasped for deployment of the next ligature loop.

Figure 23:
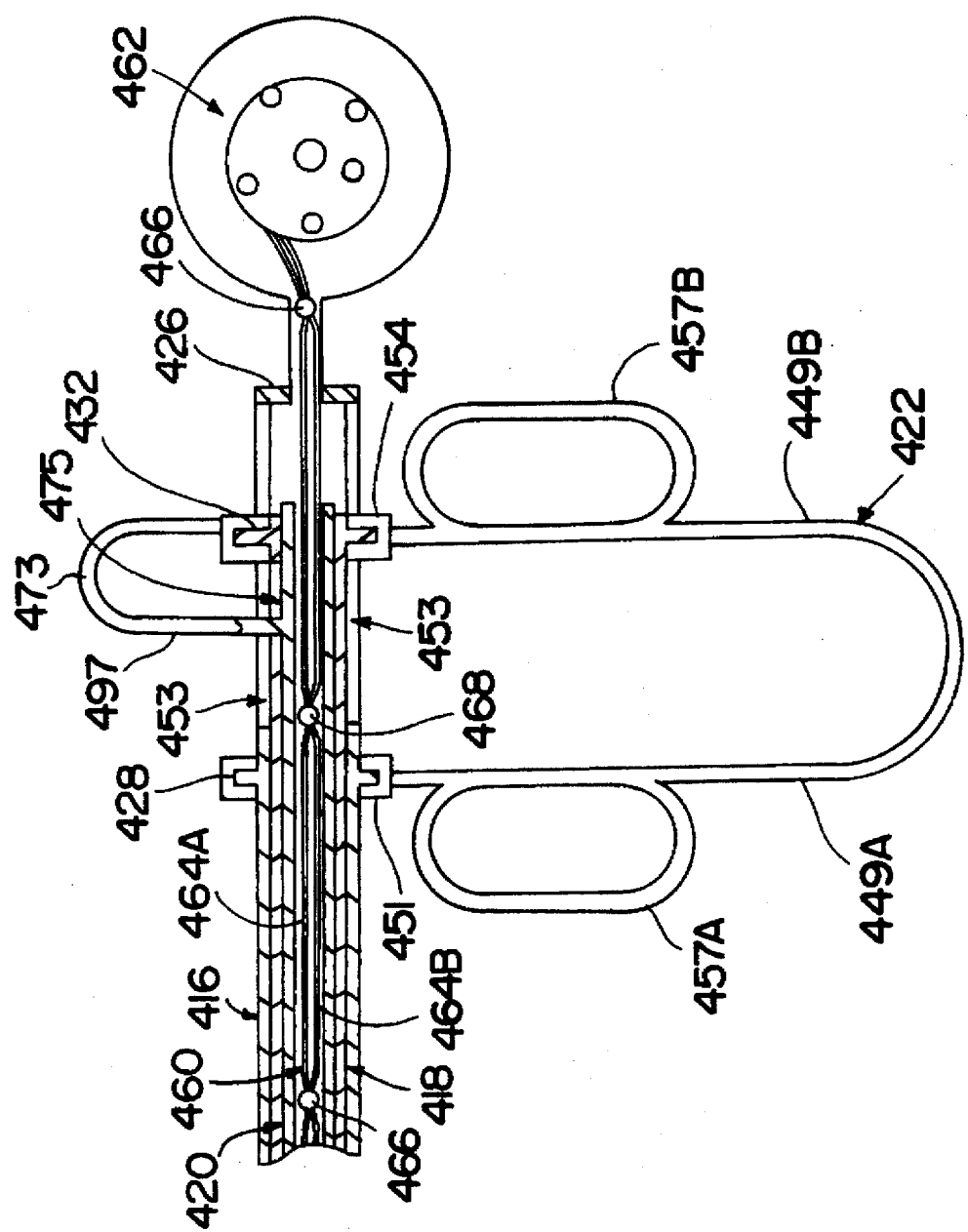
FIG. 23 is a broken side view, partly in section, of a modification of a handle arrangement for the ligating instruments of the present invention.

FIG. 23 illustrates an alternative handle arrangement for the ligating instruments according to the present invention. FIG. 23 illustrates a U-shaped handle 422 including a forward handgrip 449A connected to retention block 451 receiving flange 428 of outer member 416, the flange 428 being disposed distally of outer member end wall 426. Handgrip 449B of handle 422 is connected to retention block 454 receiving flange 432 of middle member 418, the flange 432 passing through slots 453 in outer member 416.

A spring 473 is connected between retention block 454 and the body of cutter 420 with the spring passing through upper slot 453 and a longitudinal slot 475 in middle member 418. Spring 473 is disposed on the instrument body opposite handle 422 to form a bilateral arrangement therewith, the spring 473 forming an actuator for operation of cutter 420.

In use, handle 422 is squeezed or compressed via finger rings 457A and 457B to open the jaws at the distal end of the ligating instrument and is spread via the finger rings to forcefully move the jaws toward the closed position to fix a knotting element to segments of the ligature material. Once the ligating instrument has been backed away from a ligature formed therewith, the actuator 473 is compressed or squeezed via finger pressure against a forward finger grip 497 thereof causing movement of cutter 420 proximally relative to middle member 418. Accordingly, the cutter 420 will be moved from the non-cutting position to the cutting position to cut the lengths of ligature material proximally of the ligature as described above.

Figure 24:
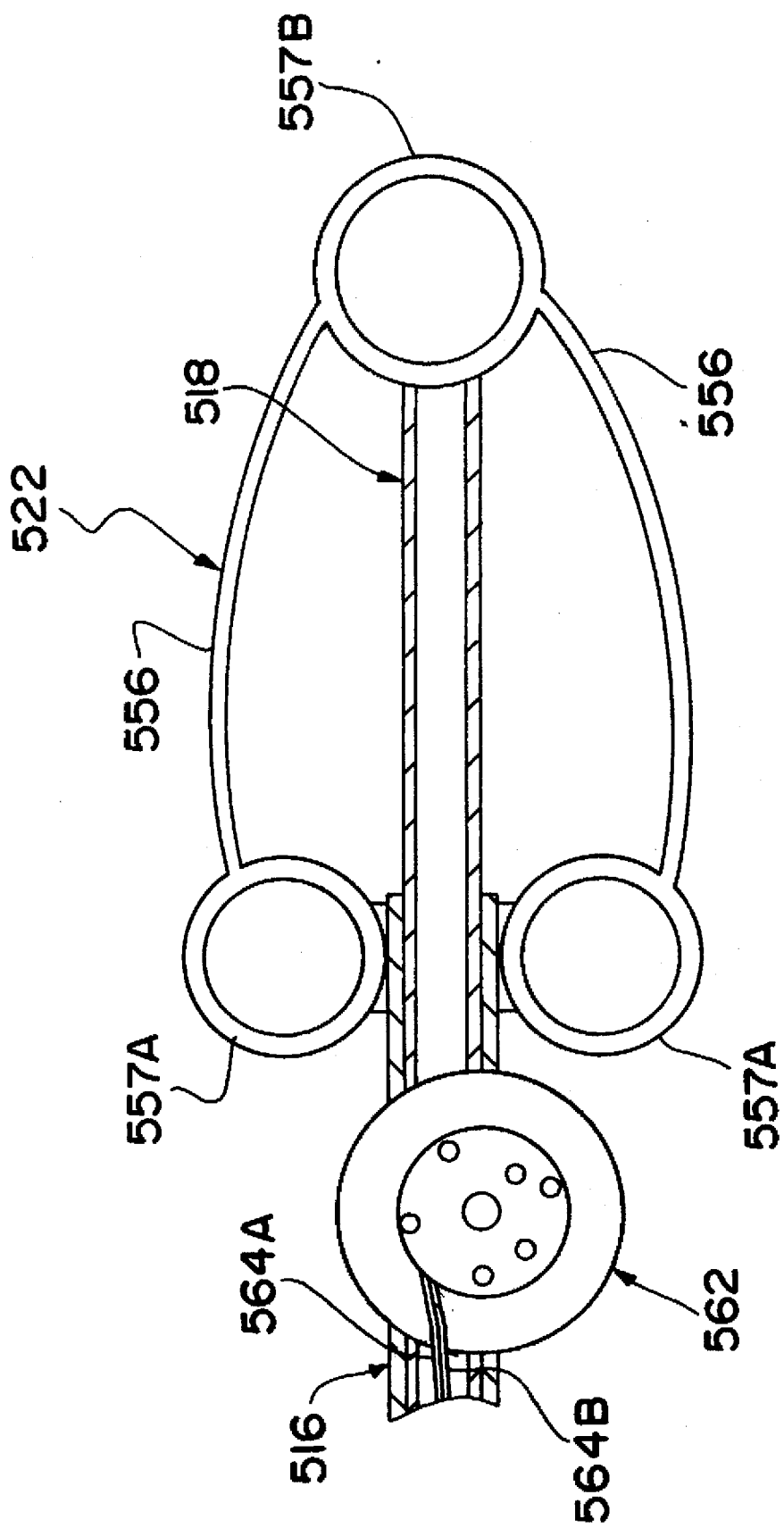
FIG. 24 is a broken side view, partly in section, of another modification of a handle arrangement as well as an alternative arrangement for the instrument body and the ligature supply for the ligating instruments of the present invention.

An alternative handle arrangement for the ligating instruments according to the present invention is illustrated in FIG. 24. FIG. 24 illustrates a handle 522 including a pair of forward finger rings 557A connected to the open proximal end of outer member 516 and a rearward thumb ring 557B connected to the proximal end of jaw member 518, the jaw member 518 extending proximally from the open proximal end of outer member 516. Forward finger rings 557A are bilaterally arranged on opposite sides of outer member 516 and are each connected to the rearward thumb ring 557B by a curved spring 556. FIG. 24 further illustrates an alternative arrangement for the instrument body and the ligature supply in that spool or operating member 562 is mounted on the instrument body forwardly of handle 522. Spool 562 is mounted externally along One side of the outer member 516, and the lengths of ligature material 564A and 564B enter the instrument body through aligned slots or openings in the lateral walls of the outer member and jaw member. ° 20 Use of handle 522 is similar to that described above in that the handle is squeezed by moving the forward finger rings 557A toward the rearward thumb ring 557B and/or moving the rearward thumb ring 557B toward the forward finger rings 557A to open the jaws at the distal end of the instrument. The handle is spread by moving the forward finger rings 557A away from the rearward thumb ring 557B and/or moving the rearward thumb ring 557B away from the forward finger rings 557A to forcefully move the jaws toward the closed position to fix a knotting element to segments of the ligature material.

An alternative handle arrangement as well as an alternative arrangement for the instrument body and ligature supply for the ligating instruments according to the present invention is illustrated in FIG. 25. The arrangement shown in FIG. 25 is similar to that shown in FIG. 22 except that spool or operating member 662 illustrated in FIG. 25 is mounted on the instrument body opposite the handle in a bilateral arrangement therewith. Handle 622 illustrated in FIG. 25 is similar to handle 322 and includes a forward handgrip 649A connected with retention block 651 having a recess therein receiving flange 632 of jaw member 618, the flange 632 passing through slot 653 in the outer member 616. Handle 622 includes handgrip 649B connected with a flange 628 protruding from the end wall 626 of the outer member 616. The handgrips 649A and 649B are connected by a spring base 631 and are provided with oblong finger rings 657A and 657B, respectively. One or more mounting bars 680 extend from an external surface of outer member 616 in a direction opposite handle 622, and spool 662 is rotatably mounted on or between the mounting bars with the lengths of ligature material 664A and 664B entering the instrument body through a hole 647 in the outer member.

An additional alternative handle arrangement for the ligating instruments of the present invention is illustrated in FIG. 26 and includes handle 722 comprising a pair of bilaterally arranged U-shaped handles 722' and 722", each of which includes a forward handgrip 749A' and 749A", respectively, and a rearward handgrip 749B' and 749B", respectively, connected to the forward handgrip by a spring base 731' and 731", respectively. Forward handgrips 749A' and 749A are connected with retention block 751 having a recess therein receiving flange 732 at the proximal end of jaw member 718, the flange 732 passing through longitudinal slots 753 in outer member 716. Handgrips 749B' and 749B are connected or formed integrally with end wall 726 of outer member 716 with the handle normally disposed in a rest position as shown. A locking arm 791 extends distally from rearward handgrip 749B' parallel or substantially parallel with a longitudinal axis of the ligating instrument, the locking arm 791 passing through an aperture 792 in the corresponding forward handgrip 749A'. The locking arm 791 terminates distally at an enlarged finger button 793 and carries or is provided with a plurality of locking teeth 795 for engaging corresponding locking structure in the surface of handgrip 749A' defining aperture 792. The locking arm 791 is manually pivotable downwardly within aperture 792 by means of finger button 793 to selectively move the locking teeth 795 out of engagement with the locking structure of aperture 792 to unlock the handle 722 for movement to a desired spread or squeezed position. Upon release of finger button 793, locking arm 791 will be returned to the locked position with teeth 795 in engagement with the locking structure of aperture 792. Accordingly, handle 722 can be locked in various incremental spread or squeezed positions. Spool 762 is mounted forwardly of handle 722 on one side of the outer member 716 as previously described for the arrangement of FIG. 24.

A modification of a knotting element 868 for use as a fixed knotting element or a movement permitting knotting element in the ligature supplies of the present invention is illustrated in FIG. 27. Knotting element 868, which is shown as a movement permitting knotting element, is similar to knotting element 68 except that the juxtaposed passages receiving the lengths of ligature material are designed to permit movement of the lengths of ligature material therethrough in only one direction. Only one passage 870B is visible in FIG. 27 receiving the length of ligature material 864B. A plurality of barbs, protrusions or whiskers 894 protrude inwardly from the wall or surface of the knotting element body defining passage 870B, and the barbs extend or are angled slightly in a rearward or proximal direction. Accordingly, the length of ligature material 864B can be moved or pulled rearwardly or proximally through the knotting element 868 but cannot be moved forwardly or distally through the knotting element 868 due to barbs 894. With the knotting element 868, the lengths of ligature material can be pulled to tighten or reduce the size of the ligature loop to a desired tension at which time the tensioned ligature loop will be secured since the knotting element and segments of ligature material in the passages of the knotting element cannot move in a direction to cause untightening or expansion of the size of the ligature loop. Where the knotting element 868 is utilized as the movement permitting knotting element, plastic deformation of the knotting element to secure the ligature may not be necessary but may be desirable to provide a double lock for redundant securement or protection.

An alternative knotting element for use in the ligature supplies according to the present invention is illustrated at 968 in FIG. 28. The knotting element of FIG. 28 can be designed as a fixed knotting element or a movement permitting knotting element, a movement permitting knotting element 968 being shown. Knotting element 968 is similar to knotting element 68 except that passages 970A and 970B are arranged differently in knotting element 968 and knotting element 968 is spring loaded to be normally disposed in a closed position. Passages 970A and 970B receiving lengths of ligature material 964A and 964B, respectively, extend longitudinally through legs 972 to be disposed on opposite sides of mouth 971. Knotting element 968 is normally disposed in a closed position with mouth 971 closed or substantially closed with the inner surfaces of the legs 972 in contact or substantially in contact with one another while allowing movement of the lengths of ligature material relative to the knotting element. Knotting element 968 is spring loaded to be movable from the closed position to an open position wherein mouth 971 is open to receive segments of one or more lengths of ligature material between legs 972. Knotting element 968 is biased for movement from the open position to the closed position automatically upon release of an opening force thereon to grip the segments of ligature material between legs 972. In use, the knotting element can be opened with a separate grasping instrument or forceps, or the segments of ligature material can be slid into the mouth 971 with the knotting element in the closed position, or the jaws of the ligating instrument can be designed in many various ways to be operated by the handles to selectively open the knotting elements 968 as disclosed in applicant's prior application Ser. No. 08/401,002, incorporated herein by reference. Various ways in which segments of filamentous material can be positioned in the mouth of a knotting element to be held thereby are disclosed in applicant's prior application Ser. No. 08/366,285, Ser. No. 08/377,723 and Ser. No. 08/401,002 incorporated herein by reference. For example, the knotting element can be fixed to the lengths of ligature material to secure a ligature by positioning segments of the lengths of ligature material extending proximally from the knotting element in the mouth thereof. Where the spring force of the knotting element is sufficient to secure the ligature by gripping the segments of ligature material between legs 972, plastic deformation of the knotting element is not required. However, for additional protection or securement, the passages 970A and 970B can be provided with barbs or whiskers for one-way movement of the lengths of ligature material therethrough as described above and/or the knotting element 968 can be plastically deformed for movement to a second or further closed position to secure the ligature by crushing the knotting element to grip the lengths of ligature material in passages 970A and 970B. Accordingly, two segments of each length of ligature material will be fixed to the knotting element, i.e. a first segment in one of the passages and a second segment between legs 972.

FIG. 29 illustrates another modification of a knotting element for use as a fixed knotting element or a movement permitting knotting element in the ligature supplies according to the present invention. FIG. 29 illustrates a movement permitting knotting element 1068 similar to knotting element 968 except that knotting element 1068 is not spring loaded and includes structure for locking the knotting element in a closed, compressed position. Passages 1070A and 1070B receiving lengths of ligature material 1064A and 1064B, respectively, are arranged in knotting element 1068 in the same manner as passages 970A and 970B. Knotting element 1068 is normally disposed in an open position with legs 1072 separated from one another to define a mouth 1071 between inner surfaces 1074 thereof. One of the legs 1072 includes a locking protrusion 1096 and the other leg 1072 includes a notch 1098 for receiving the protrusion 1096 in locking engagement therewith when the knotting element 1068 is moved from the open position to the closed position. Use of knotting element 1068 is similar to that described for knotting element 968 in that a ligature formed with knotting element 1068 can be secured by positioning segments of the lengths of ligature material extending proximally from the knotting element in mouth 1071 and moving the knotting element from the open position to the closed position to secure the segments of ligature material between legs 1072. In the closed position for the knotting element, legs 1072 will be in contact or substantially in contact with one another and the knotting element will be locked in the closed position due to engagement of protrusion 1096 in notch 1098. For additional protection or securement, the passages of the knotting element can be provided with barbs for one-way movement of the knotting element along the lengths of ligature material and/or the knotting element can be plastically deformed to additionally grip the lengths of ligature material in passages 1070A and 1070B. Various structure for locking the knotting elements in a closed position is disclosed in prior application Ser. No. 08/366, 285, Ser. No. 08/377,723, and Ser. No. 08/401,002 incorporated herein by reference. As shown in FIG. 29, the inner surfaces 1074 of legs 1072 are knurled, serrated or configured or provided with structure for gripping the segments of the lengths of ligature material therebetween, and various gripping structure suitable for use in the knotting elements of the ligature supplies according to the present invention are disclosed in prior applications Ser. No. 08/366,285, Ser. No. 08/377,723 and Ser. No. 08/401,002 incorporated herein by reference.

Figure 31:
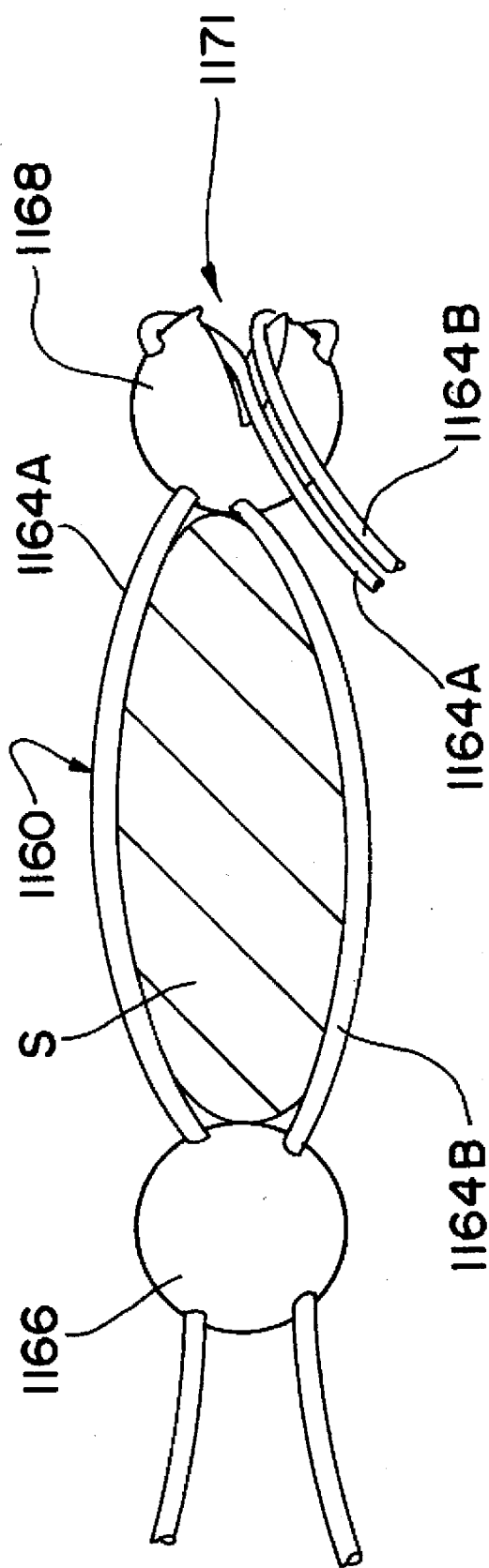
FIG. 31 is a broken perspective view illustrating one manner of use of the ligature supply of FIG. 30.

FIG. 30 illustrates a ligature supply 1114 including fixed knotting elements 1166 and movement permitting knotting elements 1168, only one of which is shown. Knotting element 1166 is similar to knotting element 66 except that passages 1069A and 1069B of knotting element 1166 fixedly receiving the lengths of ligature material 1164A and 1164B are arranged in the body of the knotting element in a criss-cross manner. Knotting element 1168 is similar to knotting element 1068 and permits movement of the lengths of ligature material 1164A and 1164B in passages 1070A and 1070B. One manner of use of ligature supply 1114 is illustrated in FIG. 31 wherein it is seen that subsequent to formation of a ligature with ligature loop 1160, segments of the lengths of ligature material 1164A and 1164B extending proximally from the knotting element 1168 are positioned in the mouth 1171 of knotting element 1168 prior to the knotting element being moved to the closed position. Once the segments of the lengths of ligature material have been positioned in the mouth of the knotting element 1168, the jaws of the ligating instrument are used to move the knotting element to the closed position wherein the segments of the lengths of ligature material in mouth 1071 are gripped by legs 1172 to secure the ligature.

FIG. 32 illustrates a distal portion of a ligating instrument incorporating a ligature supply that is similar to the ligature supply of FIG. 30 except that the mouths 1171 of the knotting elements 1168 of the ligature supply shown in FIG. 32 are oriented to face laterally rather than rearwardly or proximally. As shown in FIG. 32, subsequent to formation of a ligature in anatomical structure S with ligature loop 1160', the spool or operating member (not shown) of the ligating instrument is rotated to unwind the lengths of ligature material 1164A and 1164B allowing segments of the lengths of ligature material extending proximally from the knotting element 1168' to be positioned in the mouth 1171' thereof. The segments of ligature material can be positioned in mouth 1171' with a separate grasping instrument and/or by manipulating the knotting element 1168' to receive the segments via the jaws 1130. FIG. 33 illustrates jaws 1130 of jaw member 1118 moved toward the closed position by outer member 1116 to move knotting element 1168' from the open position to the closed position causing the ligature material segments to be secured between legs 1172' to secure the ligature. If desired, the knotting element 1168' can be made of plastically deformable material in which case the knotting element can be plastically deformed when the jaws are moved toward the closed position to grip the lengths of ligature material in the passages of the knotting element for additional securement. When the knotting element 1168' is positioned between the jaws with mouth 1171' facing the notch or recess defined by the lateral edges along one side of the jaws as described for jaws 30, the notch or recess provides enhanced visualization of the knotting element to facilitate positioning of the segments of ligature material therein as is particularly useful in multiple puncture endoscopic procedures.

Another modification of a knotting element usable as a fixed knotting element or a movement permitting knotting element in the ligature supplies of the present invention is illustrated in FIG. 34. FIG. 34 illustrates a movement permitting knotting element 1468 in the nature of a generally V-shaped clip defining opposed legs 1472 connected by a curved base 1409. A locking protrusion 1496 extends inwardly from a distal end of one of the legs 1472, the protrusion 1496 extending toward the other leg 1472 and being angled proximally in the direction of base 1409. The other leg 1472 terminates distally at an angled end 1498 for being lockingly engaged with the protrusion 1496 when the knotting element 1468 is moved to a closed position. As shown in. FIG. 34, knotting element 1468 is normally disposed in an open position with legs 1172 spaced from one another to define mouth 1171 therebetween. Recesses 1479A and 1479B are formed along inner opposed surfaces 1474 of legs 1172, respectively, for receiving segments of the lengths of ligature material 1464A and 1464B, respectively. The segments of ligature material protrude beyond inner surfaces 1474 into mouth 1471 to be disposed in contact with one another such that the ligature material segments are held between legs 1172 while allowing movement of the lengths of ligature material relative to the knotting element when the knotting element is in an open position. As shown, the lengths of ligature material pass through the knotting element in a direction transverse to legs 1172; however, the lengths of ligature material can pass through the knotting element in many various directions. As shown in FIG. 35, knotting element 1468 is movable by the jaw member of a ligating instrument from the open position to a closed position wherein legs 1172 are moved inwardly toward one another. In the closed position for knotting element 1468, inner surfaces 1474 are in contact or substantially in contact with one another to grip the lengths of ligature material 1464A and 1464B between legs 1172 to fix the knotting element relative to the ligature material to secure a ligature. Knotting element 1468 is maintained, secured or locked in the closed position due to engagement of angled end 1498 by protrusion 1496.

Another modification of a knotting element usable as a fixed or movable knotting element in the ligature supplies according to the present invention is shown at 1568 in FIG. 36. Knotting element 1568 is a movable knotting element and includes opposed legs 1572 connected by a curved base 1509. As shown in FIGS. 36 and 37, legs 1572 have a partial oval contour with curved outer surfaces and inner opposed surfaces 1574 merging with one another at an arcuate inner edge at base 1509. A locking protrusion 1596 extends inwardly from a distal end of one of the legs 1572 and is angled proximally toward base 1509. The other leg 1572 terminates distally at an angled end surface 1598. A plurality of locking teeth 1511 are formed on end surface 1598 and a plurality of locking teeth 1513 are formed on an inner surface of protrusion 1596 for lockingly engaging teeth 1511 when the knotting element 1568 is moved to a closed position as explained below. Lugs 1515 protrude from inner surfaces 1574, respectively, and a recess 1517 is provided in each inner surface 1574 opposite a lug 1515 and in alignment therewith such that each lug is received in the corresponding recess when the knotting element is in the closed position. Each lug 1515 has a passage therethrough movably receiving the lengths of ligature material 1564A and 1564B, respectively, forming a contractible ligature loop (not shown). The lengths of ligature material 1564A and 1564B extend through lugs 1515, respectively, in a direction transverse to a longitudinal axis of knotting element 1568. As best shown in FIGS. 36 and 38, inner opposed surfaces 1574 are configured with longitudinally extending ridges 1519 extending in a direction transverse to the lengths of ligature material 1564A and 1564B. The lugs 1515 and recesses 1517 are arranged such that each inner surface 1574 has a lug and a recess longitudinally aligned with one another. The lug of each inner surface is aligned with the recess of the opposing inner surface and the recess of each inner surface is aligned with the lug of the opposing inner surface.

As shown in FIGS. 36, 37 and 38, knotting element 1568 is normally disposed in an open position with inner opposed surfaces 1574 spaced from one another and lugs 1515 not received in recesses 1517. With the knotting element 1568 in the open position, the lengths of ligature material 1564A and 1564B are pulled proximally while the knotting element is held externally of the jaws of a ligating instrument to reduce the size of the ligature loop around anatomical structure to form a ligature. In order to fix the position of knotting element 1568 to secure the ligature, the jaws are utilized to move the knotting element to the closed position wherein legs 1572 and, therefore, opposed surfaces 1574, are moved toward one another causing lugs 1515 to enter recesses 1517 as shown in FIGS. 39 and 40. In the closed position, locking teeth 1511 are lockingly engaged with locking teeth 1513 and the lengths of ligature material 1564A and 1564B are fixedly secured to knotting element 1568 to secure the ligature. As best shown in FIG. 40 for length of ligature material 1564A, the length of ligature material 1564A is held by ridges 1519 and is bent due to the length of ligature material 1564A extending into and out of recess 1517.

Figure 41:
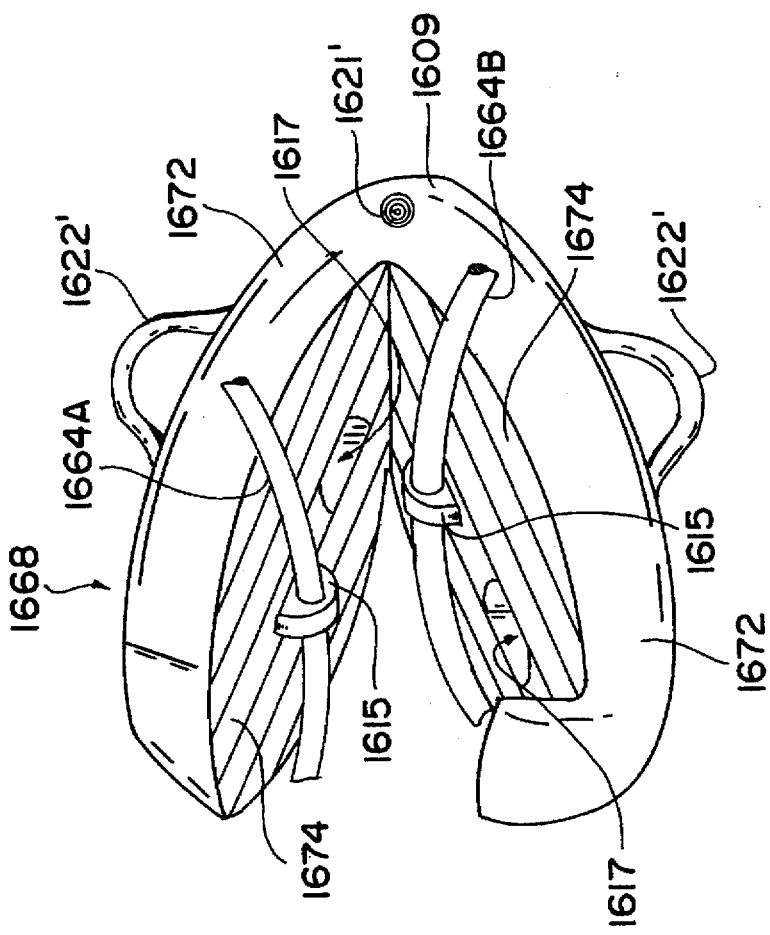
FIG. 41 is a broken perspective view of an additional modification of a knotting element for the ligature supplies according to the present invention showing the knotting element in an open position.
Figure 42:
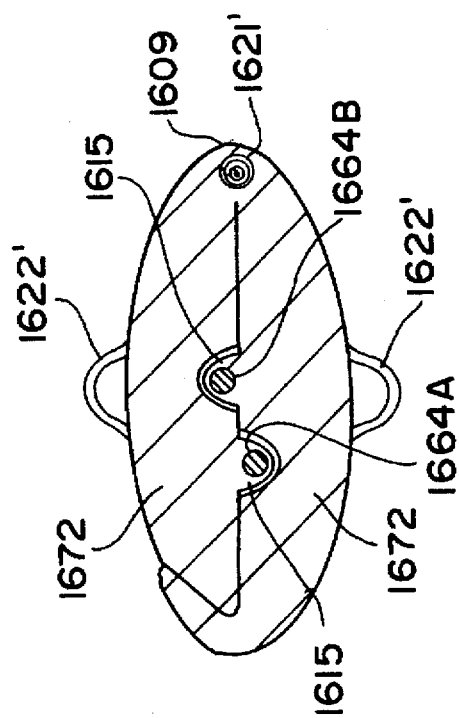
FIG. 42 is a side view of the knotting element of FIG. 41 showing the knotting element in a normally closed position.

An additional modification of a knotting element for the ligature supplies according to the present invention is illustrated in FIG. 41 wherein a movable knotting element 1668 is shown. Knotting element 1668 is similar to knotting element 1568 except that knotting element 1668 is spring-loaded to be normally disposed in the closed position shown in FIG. 42. Accordingly, knotting element 1668 includes a spring 1621', such as a coil or torsion spring, disposed at base 1609 and connected between legs 1672 to bias the knotting element to the closed position wherein inner surfaces 1674 are in contact with one another and lugs 1615 receiving the lengths of ligature material 1664A and 1664B are received in recesses 1617 such that the knotting element 1668 normally cannot move relative to the lengths of ligature material 1664A and 1664B. Engaging members 1622' in the form of protruding ears are disposed on outer surfaces of legs 1672, respectively, for being grasped by structure of the jaws of a ligating instrument to move the knotting element 1668 from the closed position to an open position shown in FIG. 41, the jaws being used to apply an opening force sufficient to overcome the closing force of spring 1621' as well as the locking force of the locking teeth where the locking teeth are provided. With the knotting element 1668 moved to the open position by the jaws, lugs 1615 will be moved out of recesses 1617 and the lengths of ligature material 1664A and 1664B will be movable relative to the knotting element 1668 allowing a ligature loop formed with the lengths of ligature material to be reduced in size to form a ligature. In order to secure the ligature, the jaws are disengaged from the engaging members 1622' causing the knotting element 1668 to return automatically to the closed position.

The instrument bodies of the ligating instruments according to the present invention can be made of any desirable medical-grade materials, such as stainless steel, to be reusable or to be disposable for single patient use. The jaws can have any desirable configuration including closed or substantially closed configurations defining a hollow interior in the closed position as well as open configurations allowing access to the interior of the jaws in the closed position. The jaws can be made of pivotally connected members as disclosed in prior application Ser. No. 08/401,002 incorporated herein by reference, which discloses jaws for opening the legs of a spring-loaded knotting element and for releasing the legs to fix the position of the knotting element relative to a length of filamentous material. The jaws can be formed integrally, unitarily with the body of the middle member or separately therefrom. The instrument body can be provided with or without a cutter depending on procedural use. The cutter can be arranged in the instrument body in many various ways and can be provided with or without nubs or bumps for camming or otherwise causing the cutter to be moved to the cutting position. Where nubs or bumps are utilized, the nubs or bumps can be disposed on the cutter or on another component or member of the instrument body, such as the jaw member. The cutter can be actuated in many ways to move to the cutting position by the hand grasping the handle, such as by actuation of the handle or a separate actuator to move the cutter or another component of the instrument body distally or proximally. Various locking mechanisms can be provided on the instrument body for selectively locking the cutter in the non-cutting position and for releasing the cutter for movement to the cutting position. Where a separate actuator is provided for actuating the cutter, the actuator can be arranged on the instrument body in many various ways to be operated by the hand grasping the handle. The cutters can be designed to cut the ligature material proximally of a ligature simultaneously with fixation of the movement permitting knotting element. The instrument bodies can include various handles, including pistol grip structure, in addition to the handles described herein. Where the handles include pivotable handgrips, both handgrips can be movable or pivotable or one of the handgrips can be movable or pivotable while the other handgrip remains stationary or fixed. Depending on the design of the instrument bodies, only slight movement of the outer member and/or the jaw member is necessary for movement of the jaws between the open and closed positions. The ligature supplies can be mounted on the instrument bodies in many various ways and at various locations to be operated by the hand grasping the handle. The operating member can be designed for manual operation to tighten a ligature loop or the operating member can be designed to tighten the ligature loop automatically as disclosed in prior application Ser. No. 08/195,491 and Ser. No. 07/930,320 incorporated herein by reference. In addition to tightening the ligature loop via the operating member, further tightening of the ligature loop can be obtained via operation of the handle to move the jaw member distally. The ligature loops can be arranged in pairs with the pairs spaced from one another such that each pair forms a double loop for being positioned around an anatomical structure for redundant securement or protection. Where more than one ligature loop is positioned around the anatomical structure, the ligature loops can be tightened together or sequentially one at a time. Various types of knotting elements can be utilized as the fixed and movement permitting knotting elements of the ligature supplies, and the knotting elements can be provided with or without a mouth. Where the knotting elements are provided with a mouth, the knotting elements can be spring-loaded such that the knotting elements are normally disposed in the closed position with the mouth thereof closed or substantially closed or the knotting elements can be non-spring loaded to be normally disposed in the open position with the mouth thereof open. The mouths of the knotting elements can be utilized to receive various types of structures desired to be secured during the course of the operative procedure. For example, the mouth of the knotting element of a first ligature loop can be utilized to receive one or more segments of ligature material forming a second ligature loop. The movement permitting knotting elements can be fixed relative to the ligature material in many various ways to secure a ligature. For example, the movement permitting knotting elements can be plastically deformed, can be moved from a normally open position to a closed position to grip one or more segments of the ligature material with or without plastic deformation or can be normally disposed in a closed position, moved to an open position to receive segments of the ligature material and returned to the closed position to grip the segments of the ligature material with or without plastic deformation. The movement permitting knotting elements can be designed to grip one segment of each length of ligature material to secure a ligature or the movement permitting knotting elements can be designed to grip more than one segment of each length of ligature material for additional securement or protection. The ligature material can pass through the knotting elements in any direction including longitudinally, laterally, and cross-wise. The mouths of the knotting elements can be arranged to face in any direction to optimally position the mouths of the knotting elements in accordance with procedural use. The knotting elements can be made of any suitable bioabsorbable or non-bioabsorbable materials, exemplary materials being titanium and polyglycolic acid. Where both the knotting elements and the ligature material are made of bioabsorbable materials, it is preferred that the materials selected have rates of absorption such that the ligature material and the knotting elements become absorbed or thinned to an insubstantial dimension at roughly the same time. For example, the lengths of ligature material, which have a smaller cross-sectional dimension than the cross-sectional dimension of the knotting elements, can be made of a material having a slower rate of absorption than the rate of absorption of the knotting elements. Where bioabsorbable materials are utilized for the knotting elements and/or the ligature material, the materials selected should have rates of absorption to ensure healing of the anatomical structure prior to absorption of the materials to an insubstantial dimension. The materials utilized for the ligature material and the knotting elements can be conventional. The knotting elements can be formed as part of the ligature material itself rather than as separate elements. A variety of ligature supplies can be made available to the surgeon for selection of the optimal ligature supply for the procedure being performed. The ligating instruments are useable in single puncture or multiple puncture endoscopic procedures, and the various instruments utilized in the ligating procedures described herein can be introduced at an internal operative site through the same or different endoscopic portals.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A ligating instrument for forming ligatures in anatomical structure at an internal operative site in the body comprising an elongate instrument body having a distal end for being introduced at the operative site, a proximal end for being disposed externally of the body and a lumen between said distal and proximal ends;

a ligature supply received within said lumen, said ligature supply being defined by lengths of filamentous ligature material carrying a plurality of fixed knotting elements and a plurality of movement permitting knotting elements arranged thereon in spaced, alternating sequence to define a plurality of ligature loops, each of said ligature loops being defined by a fixed knotting element, a movement permitting knotting element spaced from said fixed knotting element and segments of said lengths of ligature material extending between said fixed knotting element and said movement permitting knotting element, said fixed knotting elements being fixedly secured to said lengths of ligature material, said movement permitting knotting elements being slidably carried by said lengths of ligature material to permit the space between a fixed knotting element and a movement permitting knotting element of a ligature loop to be reduced in size to contract the ligature loop, said ligature loops being withdrawable through said distal end of said instrument body for positioning around anatomical structure and being contractible around anatomical structure to form ligatures; and an operating member carried by said instrument body and operable from said proximal end of said instrument body for contracting said ligature loops around anatomical structure to form ligatures.

2. A ligating instrument as recited in claim 1 wherein said operating member includes means for moving said lengths of ligature material proximally relative to said instrument body and relative to said movement permitting knotting element of a withdrawn ligature loop.

3. A ligating instrument as recited in claim 2 wherein said instrument body includes jaws at said distal end for maintaining said movement permitting knotting element of a withdrawn ligature loop externally of said instrument body when said lengths of ligature material are moved proximally by said operating member to contract the withdrawn ligature loop around anatomical structure to form a ligature.

4. A ligating instrument as recited in claim 2 wherein said operating member includes means for moving said ligature supply distally relative to said instrument body to permit withdrawal of said ligature loops through said distal end of said instrument body.

5. A ligating instrument for forming ligatures in anatomical structure at an internal operative site in the body comprising an elongate instrument body having a distal end for being introduced at the operative site, a proximal end for being disposed externally of the body and a lumen between said distal and proximal ends;

a plurality of preformed, variable size ligature loops of filamentous ligature material received within said lumen, said ligature loops being withdrawable through said distal end of said instrument body for positioning around anatomical structure and being reducible in size around anatomical structure to form ligatures;

an operating member carried by said instrument body and operable from said proximal end of said instrument body for reducing the size of said ligature loops around anatomical structure to form ligatures, said operating member including means for moving said ligature material proximally relative to said instrument body;

jaws at said distal end of said instrument body for maintaining said ligature loops externally of said instrument body when said ligature material is moved proximally by said operating member to reduce the size of said ligature loops around anatomical structure to form ligatures; and a cutter carried by said instrument body for cutting said ligature material proximally of ligatures formed with said ligature loops.

6. A ligating instrument as recited in claim 5 wherein said cutter is disposed within said lumen.

7. A ligating instrument for forming ligatures in anatomical structure at an internal operative site in the body comprising an elongate instrument body having a distal end for being introduced at the operative site, a proximal end for being disposed externally of the body and a lumen between said distal and proximal ends;

a plurality of preformed, variable size ligature loops of filamentous ligature material received within said lumen, said ligature loops being withdrawable through said distal end of said instrument body for positioning around anatomical structure and being reducible in size around anatomical structure to form ligatures; and an operating member carried by said instrument body and operable from said proximal end of said instrument body for reducing the size of said ligature loops around anatomical structure to form ligatures, said operating member including means for moving said ligature material proximally and distally relative to said instrument body, said operating member including a spool rotatable to wind and unwind said ligature material thereon.

8. A ligating instrument as recited in claim 7 and further including a handle mounting said proximal end of said instrument body and wherein said spool is mounted on said instrument body to be rotated by a hand grasping said handle.

9. A ligating instrument as recited in claim 7 and further including a rotational control mechanism for locking said spool in incremental rotational positions, said rotational control mechanism including a plurality of locking teeth carried by said spool and a pawl member carried by said instrument body for engaging said locking teeth.

10. A ligating instrument as recited in claim 9 wherein said pawl member is mounted on said instrument body in a position permitting said spool to rotate in a single direction.

11. A ligating instrument for forming ligatures in anatomical structure at an internal operative site in the body comprising an elongate instrument body having a distal end for positioning at the operative site, a proximal end for positioning externally of the body and a lumen between said distal and proximal ends;

a ligature supply including a plurality of ligature loops disposed in said lumen, said ligature loops being connected to one another in series, each of said ligature loops being withdrawable through said distal end of said instrument body for positioning around anatomical structure and including a fixed knotting element and a movement permitting knotting element carried by segments of filamentous ligature material, said fixed knotting element being fixedly secured to said segments and said movement permitting knotting element being slidably carried by said segments in a manner permitting movement of said segments of said ligature material relative to said movement permitting knotting element to tighten the ligature loop around anatomical structure;

an operating member carried by said instrument body and operable from said proximal end of said instrument body for moving said segments of said ligature material relative to said movement permitting knotting elements to tighten said ligature loops around anatomical structure to form ligatures; and a fixating member at said distal end of said instrument body for structurally deforming said movement permitting knotting elements to fixedly secure said movement permitting knotting elements to said segments of said ligature material in a manner preventing untightening of the ligatures.

12. A ligating instrument as recited in claim 11 wherein said movement permitting knotting elements are compressible and said fixating member includes jaws movable between open and closed positions to receive said movement permitting knotting elements between said jaws in said open position and to compress said movement permitting knotting elements between said jaws in said closed position such that said movement permitting knotting elements grip said segments of said ligature material.

13. A ligating instrument as recited in claim 12 wherein said movement permitting knotting elements are made of plastically deformable material and said jaws plastically deform said movement permitting knotting elements between said jaws in said closed position.

14. A ligating instrument as recited in claim 11 wherein said segments of said ligature material are movable by said operating member relative to said movement permitting knotting elements in a first direction to tighten said ligature loops and said movement permitting knotting elements each include structure preventing movement of said segments of said ligature material relative to said movement permitting knotting elements in a second direction, opposite said first direction, to prevent untightening of the ligatures formed with said ligature loops.

15. A ligating instrument as recited in claim 11 wherein each of said ligature loops includes two segments of said filamentous ligature material extending between a movement permitting knotting element and a fixed knotting element, said movement permitting knotting element connecting said two segments of ligature material to one another at a proximal end of said ligature loop and said fixed knotting element connecting said two segments of ligature material to one another at a distal end of said ligature loop.

16. A ligating instrument as recited in claim 11 wherein said ligature supply is removably disposed in said lumen of said instrument body.

17. A ligating instrument for forming ligatures in anatomical structure at an internal operative site in the body comprising an elongate instrument body having a distal end for positioning at the operative site, a proximal end for positioning externally of the body and a lumen between said distal and proximal ends;

a ligature supply including a plurality of ligature loops of filamentous ligature material disposed in said lumen, each of said ligature loops being withdrawable through said distal end of said instrument body for positioning around anatomical structure and including a movement permitting knotting element carried by said ligature material in a manner permitting movement of said ligature material relative to said movement permitting knotting element to tighten the ligature loop around anatomical structure, said movement permitting knotting elements each including opposed legs spaced from one another, said movement permitting knotting elements being compressible to move said legs toward one another;

an operating member carried by said instrument body and operable from said proximal end of said instrument body for moving said ligature material relative to said movement permitting knotting elements to tighten said ligature loops around anatomical structure to form ligatures; and a fixating member at said distal end of said instrument body for fixing said movement permitting knotting elements to said ligature material in a manner preventing untightening of the ligatures, said fixating member including jaws movable from an open position for receiving said movement permitting knotting elements to a closed position for compressing said movement permitting knotting elements to move said legs toward one another to grip said ligature material therebetween.

18. A ligating instrument as recited in claim 17 wherein said movement permitting knotting elements are made of plastically deformable material and said jaws plastically deform said knotting elements to grip said ligature material when moved from said open position to said closed position.

19. A ligating instrument for forming ligatures in anatomical structure at an internal operative site in the body comprising an elongate instrument body having a distal end for positioning at the operative site, a proximal end for positioning externally of the body and a lumen between said distal and proximal ends;

a ligature supply including a plurality of ligature loops of filamentous ligature material disposed in said lumen, each of said ligature loops being withdrawable through said distal end of said instrument body for positioning around anatomical structure and including a movement permitting knotting element carried by said ligature material, said movement permitting knotting elements each including opposed legs spring biased to be normally disposed in a closed position wherein said legs are substantially in contact with one another to grip said ligature material therebetween and prevent movement of said movement permitting knotting elements relative to said ligature material, said legs being movable away from one another against said bias to an open position permitting movement of said ligature material relative to said movement permitting knotting elements to tighten said ligature loops around anatomical structure;

an operating member carried by said instrument body and operable from said proximal end of said instrument body for moving said ligature material relative to said movement permitting knotting elements in said open position to tighten said ligature loops around anatomical structure to form ligatures; and jaws at said distal end of said instrument body movable between a jaws closed position and a jaws open position, said jaws in said jaws open position receiving said movement permitting knotting elements therebetween, said jaws in said jaws closed position engaging said legs of said movement permitting knotting elements therebetween, said jaws being movable from said jaws closed position to said jaws open position for moving said legs of said movement permitting knotting elements therebetween away from one another to permit movement of said ligature material relative to said movement permitting knotting elements between said jaws to form ligatures and being movable from said jaws open position to said jaws closed position for releasing said legs of said movement permitting knotting elements therebetween for movement to said normally closed position to grip said ligature material between said legs and prevent untightening of the ligatures.

20. A ligating instrument as recited in claim 19 wherein said knotting elements are made of plastically deformable material and said jaws plastically deform said knotting elements to grip said ligature material when moved from said jaws open position to said jaws closed position.

21. A ligating instrument for forming ligatures in anatomical structure at an internal operative site in the body comprising an elongate instrument body having a distal end for positioning at the operative site, a proximal end for positioning externally of the body, a lumen between said distal and proximal ends and a handle at said proximal end;

a ligature supply including a plurality of ligature loops of filamentous ligature material disposed in said lumen, each of said ligature loops being withdrawable through said distal end of said instrument body for positioning around anatomical structure and including a movement permitting knotting element carried by said ligature material in a manner permitting movement of said ligature material relative to said movement permitting knotting element to tighten the ligature loop around anatomical structure;

an operating member carried by said instrument body and operable from said proximal end of said instrument body for moving said ligature material relative to said movement permitting knotting elements to tighten said ligature loops around anatomical structure to form ligatures;

a fixating member at said distal end of said instrument body for fixing said movement permitting knotting elements to said ligature material in a manner preventing untightening of the ligatures; and a cutter carried by said instrument body for cutting said ligature material proximally of a ligature formed with one of said ligature loops, said fixating member and said cutter being coupled with said handle, said handle being operable to actuate said fixating member and said cutter simultaneously to fix one of said movement permitting knotting elements and to cut said ligature material proximally of said one movement permitting knotting element simultaneously.

22. A ligating instrument for forming ligatures in anatomical structure at an internal operative site in the body comprising an elongate tubular member having a distal end for being disposed at an internal operative site and a proximal end for being disposed externally of the body;

jaws at said distal end of said tubular member for being moved from a closed position wherein said jaws define a first size opening to an open position wherein said jaws define a second, greater size opening;

a handle coupled with said proximal end of said tubular member for moving said jaws between said closed position and said open position;

a plurality of preformed, contractible ligature loops of filamentous ligature material connected to one another in series and slidably disposed in said tubular member, each of said ligature loops having a knotting element of plastically deformable material attached to said ligature material, said knotting elements having a configuration to prevent passage of said knotting elements through said first size opening and to permit passage of said knotting elements through said second size opening, said ligature material being movable distally relative to said tubular member to permit movement of at least one of said ligature loops, including said knotting element thereof, distally through said second size opening with said jaws in said open position to deploy said at least one ligature loop externally of said jaws; and means disposed at said proximal end of said tubular member for moving said ligature material proximally relative to said tubular member with said jaws in said closed position to contract said at least one ligature loop around anatomical structure to form a ligature, said jaws being adapted to receive said knotting element of said at least one ligature loop between said jaws in said open position and to crush said knotting element of said at least one ligature loop between said jaws when said jaws are moved to said closed position to prevent expansion of the ligature.

23. A ligating instrument as recited in claim 22 wherein said jaws are biased toward said open position and further including an outer member disposed around said tubular member and coupled with said handle, said outer member being movable by said handle to constrain said jaws in said closed position and to release said jaws from constraint by said outer member for movement to said open position.

24. A ligating instrument for forming ligatures in anatomical structure at an internal operative site in the body comprising an elongate tubular member having a distal end for being disposed at an internal operative site and a proximal end for being disposed externally of the body;

jaws at said distal end of said tubular member for being moved from a closed position wherein said jaws define a first size opening to an open position wherein said jaws define a second, greater size opening, said jaws being biased toward said open position;

a handle coupled with said proximal end of said tubular member for moving said jaws between said closed position and said open position;

an outer member disposed around said tubular member and coupled with said handle, said outer member being movable by said handle to constrain said jaws in said closed position and to release said jaws from constraint by said outer member for movement to said open position, said outer member having an external surface and a scale along said external surface for taking measurements in the body;

a plurality of preformed, contractible ligature loops of filamentous ligature material slidably disposed in said tubular member, each of said ligature loops having a knotting element attached to said ligature material, said knotting elements having a configuration to prevent passage of said knotting elements through said first size opening and to permit passage of said knotting elements through said second size opening, said ligature material being movable distally relative to said tubular member to permit movement of at least one of said ligature loops, including said knotting element thereof, distally through said second size opening with said jaws in said open position to deploy said at least one ligature loop externally of said jaws; and an operating member disposed at said proximal end of said tubular member for moving said ligature material proximally relative to said tubular member with said jaws in said closed position to contract said at least one ligature loop around anatomical structure to form a ligature, said jaws being operable by said handle to change said configuration of said knotting element of said at least one ligature loop to prevent expansion of the ligature.

25. A ligating instrument for forming ligatures in anatomical structure at an internal operative site in the body comprising an elongate tubular member having a distal end for being disposed at an internal operative site and a proximal end for being disposed externally of the body;

jaws at said distal end of said tubular member for being moved from a closed position wherein said jaws define a first size opening to an open position wherein said jaws define a second, greater size opening;

a handle coupled with said proximal end of said tubular member for moving said jaws between said closed position and said open position;

a plurality of preformed, contractible ligature loops of filamentous ligature material slidably disposed in said tubular member, each of said ligature loops having a knotting element attached to said ligature material, said knotting elements having a configuration to prevent passage of said knotting elements through said first opening and to permit passage of said knotting elements through said second size opening, said ligature material being movable distally relative to said tubular member to permit movement of at least one of said ligature loops, including said knotting element thereof, distally through said second size opening with said jaws in said open position to deploy said at least one ligature loop externally of said jaws;

an operating member disposed at said proximal end of said tubular member for moving said ligature material proximally relative to said tubular member with said jaws in said closed position to contract said at least one ligature loop around anatomical structure to form a ligature, said jaws being operable by said handle to change said configuration of said knotting element of said at least one ligature loop to prevent expansion of the ligature; and a cutter disposed around said ligature material and having a cutting blade movable from a non-cutting position to a cutting position to cut said ligature material proximally of a ligature formed with one of said ligature loops.

26. A ligating instrument as recited in claim 25 wherein said cutter has a proximal end coupled with said handle, said handle being operable to move said cutter between said non-cutting position and said cutting position.

27. A method of forming ligatures in anatomical structure at an internal operative site in the body comprising the steps of providing a ligating instrument including an elongate instrument body having a distal end, a proximal end and a lumen between the distal and proximal ends, a ligature supply disposed within the lumen and an operating member disposed at the proximal end of the instrument body and connected to the ligature supply for moving the ligature supply relative to the instrument body, the ligature supply including lengths of filamentous ligature material carrying a plurality of fixed knotting elements and a plurality of movement permitting knotting elements arranged thereon in spaced, alternating sequence to define a plurality of ligature loops, each ligature loop including a fixed knotting element, a movement permitting knotting element spaced from the fixed knotting element and segments of the lengths of ligature material extending between the fixed knotting element and the movement permitting knotting element, the fixed knotting elements being fixedly secured to the lengths of ligature material, the movement permitting knotting elements being movably carried by the lengths of ligature material to permit movement of the ligature material relative thereto to reduce the size of the ligature loops when the ligature supply is moved proximally relative to the instrument body;

introducing the distal end of the instrument body at the internal operative site;

withdrawing a ligature loop from the distal end of the instrument body to position the ligature loop, including the knotting elements therefor, externally of the instrument body;

positioning the ligature loop around anatomical structure;

moving the operating member to move the ligature supply proximally relative to the instrument body while the movement permitting knotting element of the ligature loop is held externally of the instrument body to reduce the size of the ligature loop around the anatomical structure to form a ligature; and withdrawing another ligature loop from the distal end of the instrument body to form another ligature at the operative site without withdrawing the ligating instrument from the body.

28. A method of forming ligatures as recited in claim 27 and further including, prior to said step of withdrawing another ligature loop, fixedly securing the movement permitting knotting element of the ligature loop to the ligature material to secure the ligature.

29. A method of forming ligatures as recited in claim 28 and further including, subsequent to said step of fixedly securing, cutting the ligature material proximally of the ligature.

30. A method of forming ligatures in anatomical structure at an internal operative site in the body comprising the steps of providing a ligating instrument including an elongate instrument body having a distal end, a proximal end and a lumen between the distal and proximal ends, a ligature supply including a plurality of preformed ligature loops of filamentous ligature material disposed within the lumen and an operating member disposed at the proximal end of the instrument body and connected to the ligature material for moving the ligature material relative to the instrument body, each ligature loop including a knotting element permitting movement of the ligature material relative thereto to reduce the size of the ligature loop when the ligature material is moved proximally relative to the instrument body;

introducing the distal end of the instrument body at the internal operative site;

withdrawing a ligature loop from the distal end of the instrument body to position the ligature: loop, including the knotting element therefor, externally of the instrument body;

positioning the ligature loop around anatomical structure;

moving the operating member to move the ligature material relative to the instrument body while the knotting element of the ligature loop is held externally of the instrument body to reduce the size of the ligature loop around the anatomical structure to form a ligature;

fixing the knotting element of the ligature loop to the ligature material to secure the ligature and, simultaneously with said step of fixing, cutting the ligature material proximally of the ligature; and withdrawing another ligature loop from the distal end of the instrument body to form another ligature at the operative site without withdrawing the ligating instrument from the body.

* * * * *